United States Patent
Kikawada et al.

(10) Patent No.: US 7,892,789 B2
(45) Date of Patent: Feb. 22, 2011

(54) METHOD OF INCREASING CELL PERMEABILITY TO TREHALOSE BY RECOMBINANTLY PRODUCING A TREHALOSE TRANSPORTER

(76) Inventors: Takahiro Kikawada, c/o National Institute of Agrobiological Sciences, Ohwashi 1-2, Tsukuba, Ibaraki 305-8634 (JP); Takashi Okuda, c/o National Institute of Agrobiological Sciences, Ohwashi 1-2, Tsukuba, Ibaraki 305-8634 (JP); Masahiko Watanabe, c/o National Institute of Agrobiological Sciences, Ohwashi 1-2, Tsukuba, Ibaraki 305-8634 (JP); Ayako Saito, c/o National Institute Agrobiological Sciences, Ohwashi 1-2, Tsukuba, Ibaraki 305-8634 (JP); Yasushi Kanamori, c/o National Institute of Agrobiological Sciences, Ohwashi 1-2, Tsukuba, Ibaraki 305-8634 (JP); Yuichi Nakahara, c/o National Institute of Agrobiological Sciences, Ohwashi 1-2, Tsukuba, Ibaraki 305-8634 (JP)

( * ) Notice: Subject to any disclaimer, the term of this patent is extended or adjusted under 35 U.S.C. 154(b) by 0 days.

(21) Appl. No.: 12/073,457

(22) Filed: Mar. 5, 2008

(65) Prior Publication Data
US 2009/0111176 A1 Apr. 30, 2009

Related U.S. Application Data

(60) Provisional application No. 60/904,785, filed on Mar. 5, 2007.

(51) Int. Cl.
*C12P 21/06* (2006.01)
(52) U.S. Cl. .................................. 435/69.1
(58) Field of Classification Search .............. None
See application file for complete search history.

(56) References Cited

U.S. PATENT DOCUMENTS
2005/0186185 A1* 8/2005 Conrad et al. ............. 424/93.21

FOREIGN PATENT DOCUMENTS
JP 2000-038343 A 2/2000

OTHER PUBLICATIONS

Kikawada et al., "Trehalose transporter 1, a facilitated and high-capacity trehalose transporter, allows exogenous trehalose uptake into cells", Proc. Natl. Acad. Sci. U.S.A. 104:11585-11590, 2007.*
Kizana et al., Heart, Lung and Circulation 2007;16:180-184.*
Nishizaki, Y., et al. (2000) Nutrition Research 20, 653.
Tanaka, M. et al. (2004) Nat Med 10, 148-154.
Crowe, J. H., et al. (1987) Biochem J 242, 1-10.
Crowe, J. H., et al. (1988) Annu Rev Physiol 60, 73-103.
Wolkers, W. F., et al. (2001) Cryobiology 42, 79-87.
Guo, N., et al. (2000) Nat Biotechnol 18, 168-171.
Eroglu, A., et al. (2000) Nat Biotechnol 18, 163-167.
Oliver, A. E., et al. (2004) Cell Preservation Technology 2, 35-49.
Boos, W., et al. (1998) Microbiol Mol Biol Rev 62, 204-229.
Stambuk, B. U., et al. (1996) Eur J Biochem 237, 876-881.
Brumfiel, G., (2004) Nature 428, 14-15.
Davies JE, et al. (2006) Hum Mol Genet. 15 (23-31).
Elliott GD, et al. (2006) Cryobiology 52, 114-127.
Elbein, A. D., et al. (2003) Glycobiology 13, 17R-27R.
Crowe, J. H., et al. (2005) Integr Comp Biol 45, 810-820.
Benaroudj, N., et al. (2001) Biol Chem 276, 24261-24267.
Couzin, J., (2004) Science 304, 816-817.
GeneBank No. P68187; TC: 3.A1.1 , Oct. 13, 2009.
GeneBank No. P53048; TC: 2.A.1.1.11 , Oct. 13, 2009.
Stambuk, B. U., et al (1999) FEMS Microbiol Lett 170, 105-110.

* cited by examiner

*Primary Examiner*—David J Steadman
(74) *Attorney, Agent, or Firm*—Kubotera & Associates LLC

(57) ABSTRACT

There are provided trehalose transporter gene and a method of introducing trehalose into cells by using the gene. Candidates for the trehalose transporter genes were searched in *P. vanderplanki* EST, resulting in being obtained cDNA designated as Tret1. Tret1 encodes a 504 amino acid protein with 12 transmembrane structures. Tret1 expression was induced by desiccation stress and predominant in the fat body. Functional expression of TRET1 in *Xenopus* oocytes showed that transport activity was specific for trehalose and independent of extracellular pH and electrochemical membrane potential. The direction of transport of TRET1 was reversible depending on the concentration gradient of trehalose. Apparent Km and Vmax of TRET1 for trehalose were extraordinarily high values. These results indicate that TRET1 is a facilitated, high-capacity trehalose-specific transporter. Tret1 is widespread in insects. Furthermore, TRET1 conferred trehalose permeability upon cells including those of vertebrates as well as insects.

1 Claim, 10 Drawing Sheets

Predicted structure of PvTRET1

Hours of desiccation
0 1 3 6 24 48

*PvTRET1*

EtBr

Antisense

Sense

METHOD OF INCREASING CELL PERMEABILITY TO TREHALOSE BY RECOMBINANTLY PRODUCING A TREHALOSE TRANSPORTER

CROSS-REFERENCE TO RELATED APPLICATIONS

The application claims the benefit under 35 U.S.C. 119(e) of the provisional application No. 60/904,785, filed on Mar. 5, 2007.

REFERENCE TO SEQUENCE LISTING

The Sequence Listing is submitted on a compact disc, labeled as "Copy 1", which is incorporated in the application by reference. A duplicate copy of the compact disc, labeled as "Copy 2", is also submitted. The Sequence Listing is stored by a file name "sequences kikawada" on each of the compact discs, "Copy 1" and "Copy 2", created on Mar. 3, 2008, having the size of 65 KB. The total number of compact discs is two, and the total number of the file on each disc is one.

I hereby state that the information recorded in computer readable form is identical to the written (on paper or compact disc) sequence listing.

The Sequence Listing is submitted on a compact disc, filed on Dec. 18, 2008, which is incorporated in the application by reference. The Sequence Listing is stored by a file name "sequences kikawada1" on the compact disc, created on Dec. 4, 2008, having the size of 68 KB. The total number of compact disc is one, and the total number of the file on the disc is one.

I hereby state that the information recorded in computer readable form is identical to the written (on paper or compact disc) sequence listing.

FIELD OF THE INVENTION

The present invention relates to trehalose transporter gene and method of introducing trehalose into cells by using the gene.

BACKGROUND OF THE INVENTION

Trehalose is a nonreducing disaccharide formed by an α,α-1,1-glucoside bond between two α-glucose units. It is widespread in organisms such as insects, crustaceans, fungi and bacteria, being used as their energy and carbon source. Trehalose, in contrast to reducing sugars, does not possess the toxicity caused by the Maillard reaction, which is a chemical reaction between amino acids in proteins and carbonyl group in reducing sugars and results in denaturation of the proteins (Elbein, A. D., et al. (2003) *Glycobiology* 13, 17R-27R). Moreover, trehalose has distinctive physiological properties not seen in any other sugars.

As an example, trehalose prevents osteoporosis by disturbing osteoclast differentiation (Nishizaki, Y., et al. (2000) *Nutrition Research* 20, 653). Also, it alleviates accumulation of abnormal proteins in nerve cells and muscle cells, caused by polyglutamine and polyalanine disease known as Huntington's disease (Tanaka, M., et al. (2004) *Nat Med* 10, 148-154.) and oculopharyngeal muscular dystrophy (Davies, J. E., et al. (2006) *Hum Mol Genet.* 15, 23-31), respectively. In addition, trehalose as a chemical chaperon or an antioxidant protects biomolecules such as proteins and the cellular membranes form stresses such as desiccation, heat, low temperature, and high and low oxygen (Crowe, J. H., et al. (2005) *Integr Comp Biol* 45, 810-820; Crowe, J. H., et al. (1987) *Biochem J* 242, 1-10; Crowe, J. H., et al. (1998) *Annu Rev Physiol* 60, 73-103; Elbein, A. D., et al. (2003) *Glycobiology* 13, 17R-27R; Benaroudj, N., et al. (2001) *J Biol Chem* 276, 24261-24267).

An advanced applied research on the bioactivity of trehalose is being conducted. For instance, by using trehalose as an anhydro-protectant, the Defense Advanced Research Projects Agency (DARPA) is developing a method to preserve the blood for transfusion in dry state (Brumfiel, G. (2004) *Nature* 428, 14-15). As a result, they have succeeded in preserving akaryotic platelet for almost two years by the technique that the platelets is heated to introduce trehalose into the cells through endocytosis, and then freeze-dried (Wolkers, W. F., et al. (2001) *Cryobiology* 42, 79-87).

However, platelet is so far the only successful example, since other karyotic cells have not yet been successfully desiccated. As for developing medication to cure Huntington's disease and osteoporosis for practical use (Couzin, J. (2004) *Science* 304, 816-817), not enough studies that apply the bioactivity of trehalose are being performed. These are attributed that trehalose is an impermeable molecule across the cellular membranes without heating. Hence, discovering the method to introduce trehalose into cells facilely without harming is the key to establish the uses of trehalose for basic and applied goals in karyotic cells and live bodies.

To date, several trials introducing trehalose into cells have been reported: introduction of bacterial trehalose biosynthetic enzyme genes (otsA and otsB) into cells increases intracellular trehalose (Guo, N., et al. (2000) *Nat Biotechnol* 18, 168-171); engineered switchable pores or extracellular nucleotide-gated channels were created in cellular membranes to allow trehalose uptake (Eroglu, A., et al. (2000) *Nat Biotechnol* 18, 163-167; Elliott, G. D., et al. (2006) *Cryobiology* 52, 114-127). Indeed, both techniques allow increasing intracellular concentration of trehalose. However, the former is hard to eliminate trehalose even when it is no longer necessary. This retention could cause ill effect because trehalose can prevent refolding of denatured proteins. The later enabled trehalose to move from the extracellular fluid into cells; however, undesired influx and efflux of other molecules probably occur simultaneously. In addition, introduction of trehalose into cells through spontaneous uptake such as pinocytosis has been attempted (Wolkers, W. F., et al. (2001) *Cryobiology* 42, 79-87); however, it is largely dependent on cell characteristics, so that uptake of a large amount of trehalose is not expected. Therefore, in order to easily and selectively introduce trehalose into cells, it is necessary to use trehalose-specific transporter localized in the cellular membranes.

Transporters promoting permeation of trehalose across cellular membrane have already been found from unicellular organisms such as bacteria, archaea and yeast. The transporters are active α-glucoside transporters such as MalEFGK$_2$. (GeneBank no. P68187; TC: 3.A1.1) for bacteria and archaea (Boos, W. & Shuman, H. (1998) *Microbiol Mol Biol Rev* 62, 204-229), and MAL11/AGT1 (GeneBank no. P53048; TC: 2.A.1.1.11) for yeast (Stambuk, B. U., et al. (1996) *Eur J Biochem* 237, 876-881; Stambuk, B. U., et al. (1999) *FEMS Microbiol Lett* 170, 105-110; Han, E. K., et al. (1995) *Mol Microbiol* 17, 1093-1107). However, there are no reports that these transporters are utilized for introducing trehalose into cells in higher organisms. The reasons are thought to be as follows (Boos, W. & Shuman, H. (1998) *Microbiol Mol Biol Rev* 62, 204-229; Stambuk, B. U., et al. (1996) *Eur J Biochem* 237, 876-881; Stambuk, B. U., et al. (1999) *FEMS Microbiol Lett* 170, 105-110; Han, E. K., et al. (1995) *Mol Microbiol* 17, 1093-1107). (I) Intracellular energy might be consumed because the active transporters require either ATP hydrolysis or a favorable membrane potential as driving force to transport substrates. (II) Substrate selectivity of those transporters is relatively broad and includes alpha-glucosides such as trehalose, sucrose and maltose. (III) Coordinate expression of the four different genes needed for MalEFGK$_2$ is difficult. (IV) The optimum pH for MAL11/AGT1 is acidic rather than neutral. (V) The direction of those transporters is only inward. Thus, these problems can be resolved by using the transporter that is facilitated and trehalose-specific transporter, is bidirectional between the external environment and cytosol, is governed by a single gene product, and is independent of pH and membrane potential.

The present invention was made in view of such a situation, and an objective of the present invention is to provide trehalose transporter gene and method of introducing trehalose into cells by using the gene. More specifically, the present invention provides a gene (Tret1) encoding a *P. vanderplanki*-derived facilitated trehalose transporter protein (TRET1), a vector carrying the gene, and a method for introducing trehalose into cells by using the gene.

SUMMARY OF INVENTION

To date, isolation of facilitated trehalose transporter genes has never been reported, and the present invention provides the first example of isolating facilitated trehalose transporter genes, Tret1.

That is, the present invention relates to trehalose transporter gene and method of introducing trehalose into cells by using the gene. More specifically, the present invention provides:

[1] a polynucleotide of which encodes a protein having a facilitated trehalose transport activity, wherein the polynucleotide is selected from the group consisting of:

(a) a polynucleotide encoding a protein comprising the amino acid sequence of SEQ ID NO: 2, (b) a polynucleotide comprising a coding region of the nucleotide sequence described in SEQ ID NO: 1, (c) a polynucleotide encoding a functionally-equivalent protein to a protein comprising the amino acid sequence of SEQ ID NO:2 with one or more amino acid substitutions, deletions, additions, and/or insertions in the amino acid sequence of SEQ ID NO: 2, (d) a polynucleotide that hybridized under highly stringent conditions with a complementary strand of a polynucleotide comprising the nucleotide sequence of SEQ ID NO: 1, and (e) a polynucleotide encoding a functionally-equivalent protein to a 12-transmembrane protein comprising the amino acid sequence of SEQ ID NO:2 with one or more amino acid substitutions, deletions, additions, and/or insertions in the amino acid sequence of SEQ ID NO: 2;

(f) a polynucleotide encoding a protein comprising amino acid sequence of SEQ ID NO: 11 with one or more amino acid substitutions, deletions, additions, and/or insertions in the amino acid sequence of SEQ ID NO: 2.

[2] a vector comprising the polynucleotide of [1];

[3] a transformed cell carrying the polynucleotide of [1]

[4] a transformed cell retaining the vector of [2];

[5] a protein encoded by the polynucleotide of [1];

[6] a method for conferring increase of permeability for trehalose across the cellular membrane to a cell, wherein the method comprises in the cell a protein encoded by the polynucleotide of [1];

[7] a method for introducing trehalose into a cell, wherein the method comprises in the cell a protein encoded by the polynucleotide of [1].

The present inventors succeeded in isolating novel genes encoding a facilitated trehalose transporter protein from insects such as *P. vanderplanki, Drosophila melanogaster, Anopheles gambiae, Apis mellifera* and *Bombyx mori*. The present invention provides trehalose transporter gene and method of introducing trehalose into cells by using the gene. Thereby, the present invention allows trehalose uptake easily into cells by expressing insect Tret1 gene.

DETAILED DESCRIPTION OF THE INVENTION

Hereinafter, details of the present invention will be described according to tables.

The present inventors attempted to isolate unidentified and novel facilitated trehalose transporter from an African chironomid, *P. vanderplanki* that extremely accumulates trehalose upon desiccation (Watanabe, M., et al. (2002) *J Exp Biol* 205, 2799-2802; Watanabe, M., et al. (2003) *J Exp Biol* 206, 2281-2286; Kikawada, T., et al. (2005) *Integr Comp Biol* 45, 710-714). Specifically, candidates for the trehalose transporter genes were searched in our original *P. vanderplanki* EST, resulting in identifying a subset of six EST clones that form a single cluster annotated as a sugar transporter. Based on these data, and followed by 5'- and 3'-RACE, the inventors obtained full-length cDNA (~2.3 kb) designated as Tret1 (Trehalose transporter 1 gene) (FIG. 1A).

Tret1 cDNA possesses a single open reading frame (ORF) encoding a 55-kDa protein of 504 amino acids (FIG. 1A).

Figure 1:
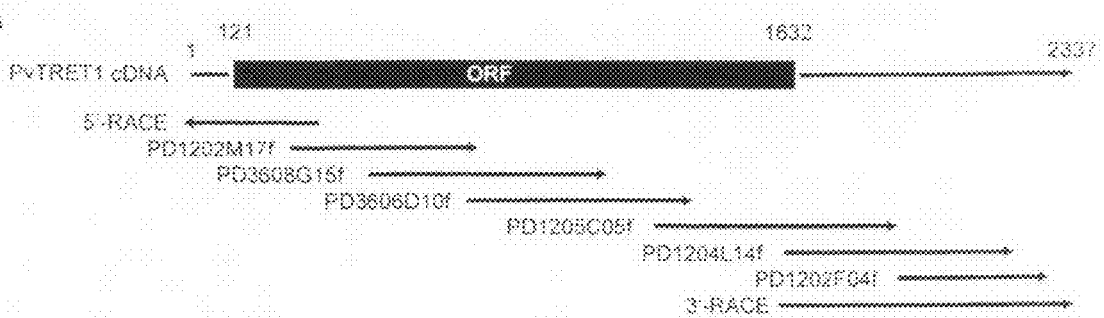
FIG. 1 shows structure of the TRET1 gene and protein. (A) Cloning of TRET1 cDNA from the sleeping chironomid (*Polypedilum vanderplanki*). (B) BLASTP search showed that translation product of TRET1 presumably has a conserved domain of a sugar transporter. (C) Topological model for the structure of the TRET1 protein.
Figure 1:
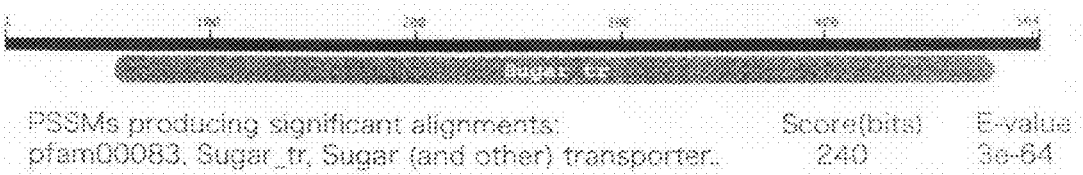
Figure 1:
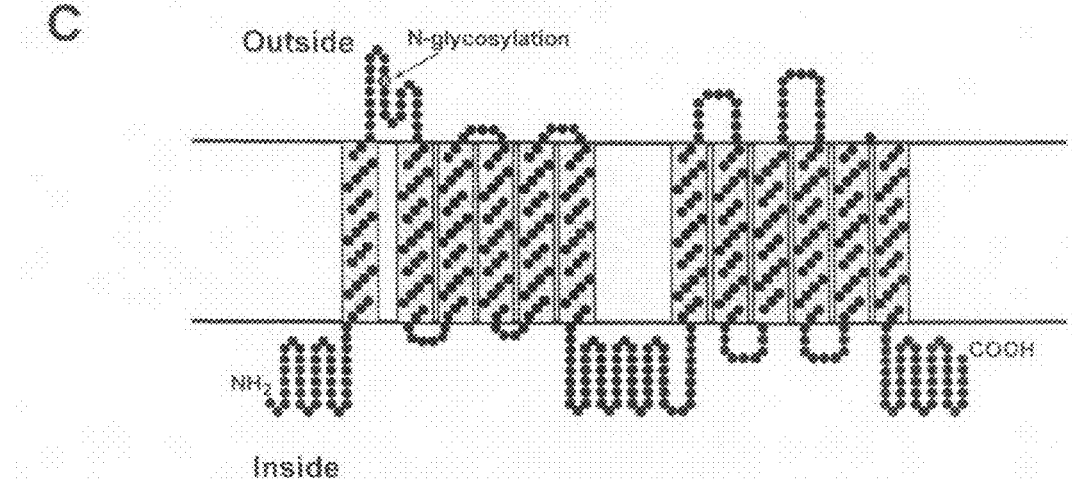
Figure 2:
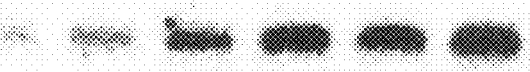
FIG. 2 is a photograph showing that expression of Tret1 gene is induced by desiccation stress in larvae of *P. vanderplanki*. EtBr staining shows 28S rRNA after electrophoresis.
Figure 2:
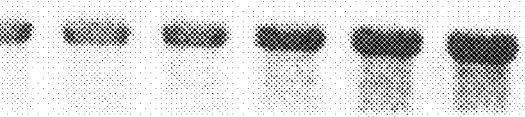

TRET1 has a domain for sugar (and other) transport (Pfam accession number: PF00083) located at amino acid residues 46 and 484 (FIG. 1B). From the prediction of secondary structure of membrane proteins using SOSUI analysis (bp-.nuap.nagoya-u.ac.jp/sosui/), TRET1 is thought to form a 12-transmembrane structure (FIG. 1C). Furthermore, upon desiccation, expression pattern of Tret1 gene was corresponded well with accumulation pattern of trehalose in larvae of *P. vanderplanki* (FIG. 2). These results suggest that TRET1 should be deeply involved in trehalose transport.

Figure 3:
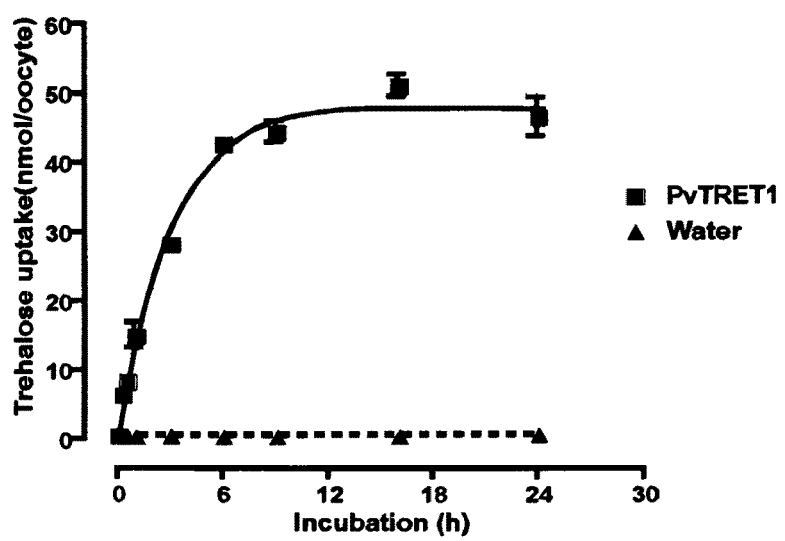
FIG. 3 shows that Tret1 gene encodes a trehalose-specific transporter. (A) Time course of trehalose uptake by *Xenopus* oocytes injected with either Tret1 cRNA or distilled water as sham. Substrate selectivities of TRET1 (B) and human GLUT1 (C) for disaccharides and glucose derivatives are also shown.
Figure 3:
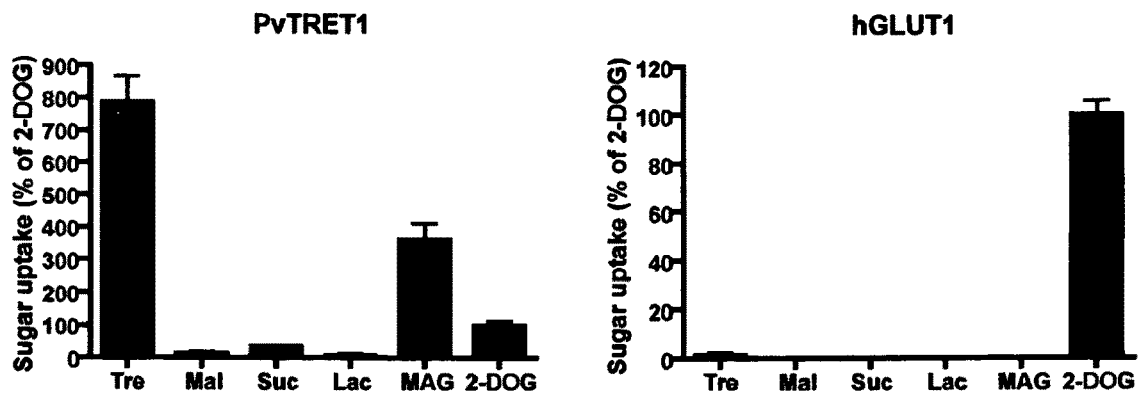
Figure 4:
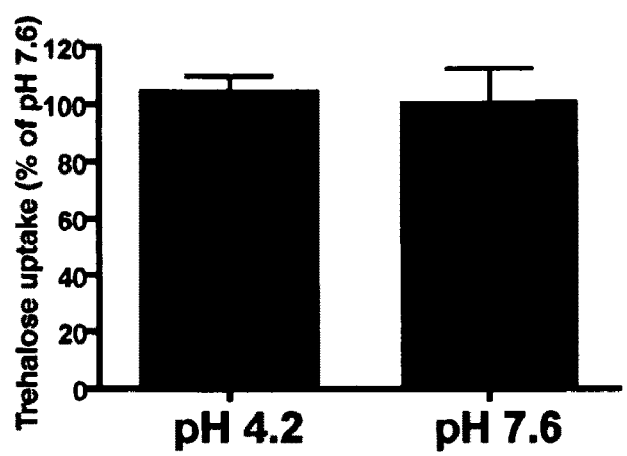
FIG. 4 shows that TRET1 is a facilitated transporter. (A) The pH-dependency of TRET1. (B) The effects of ionophores and an uncoupler on TRET1 activity.
Figure 4:
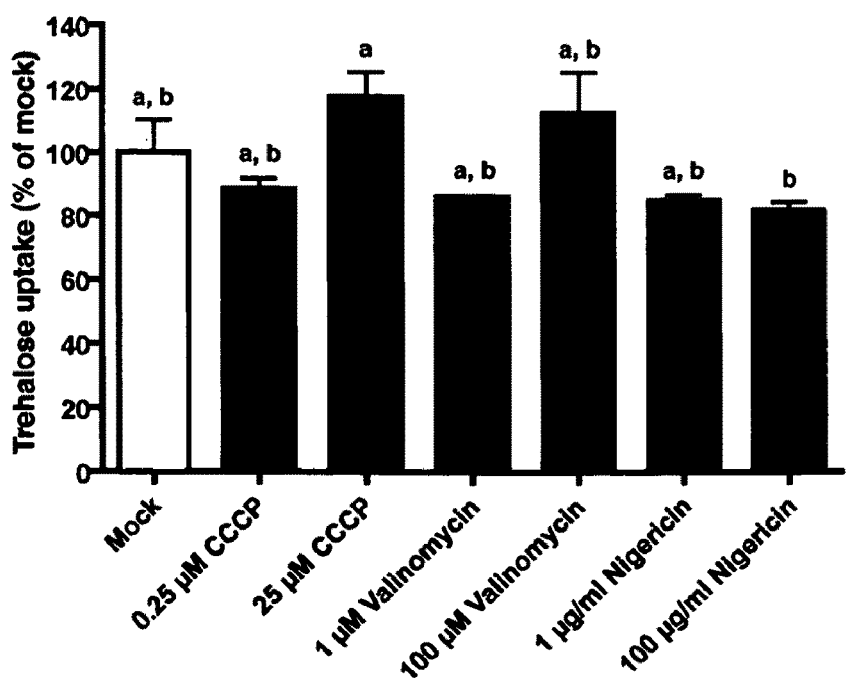
Figure 5:
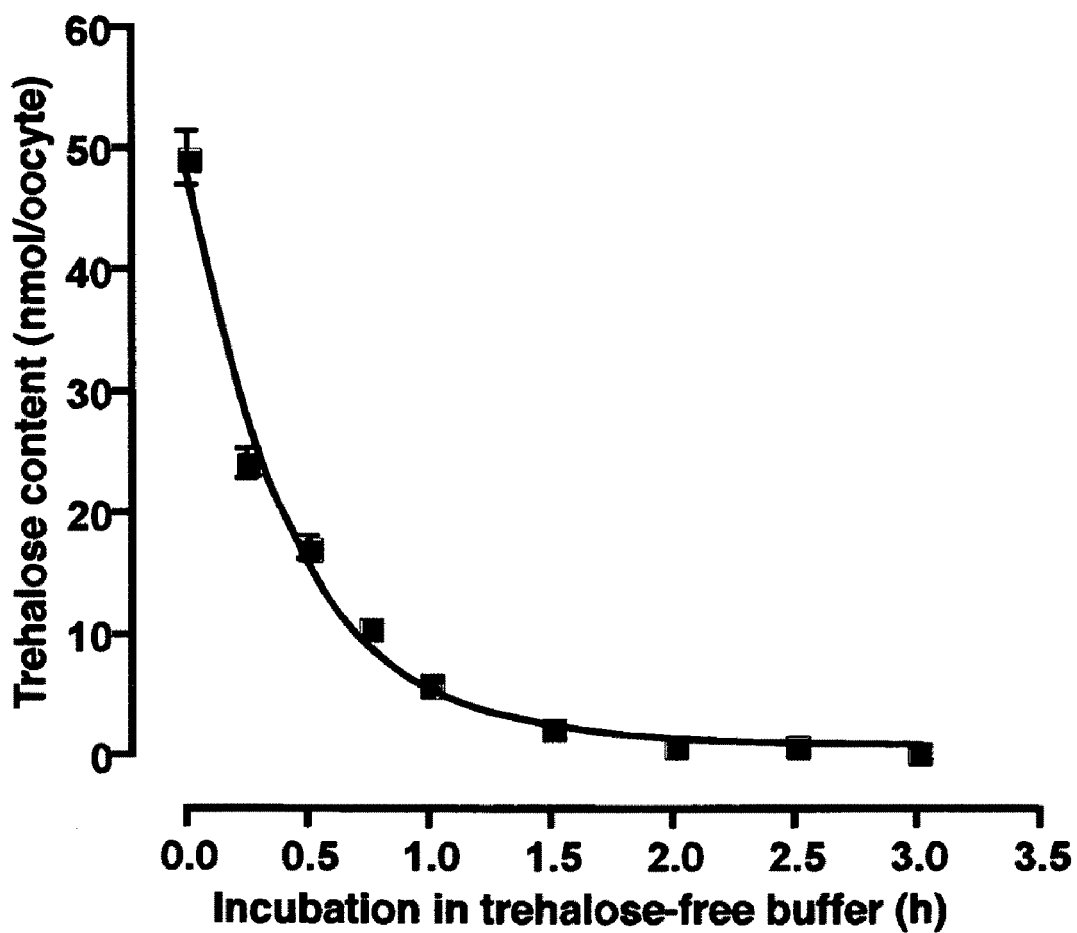
FIG. 5 shows bi-directional trehalose transport activity of TRET1.
Figure 6:
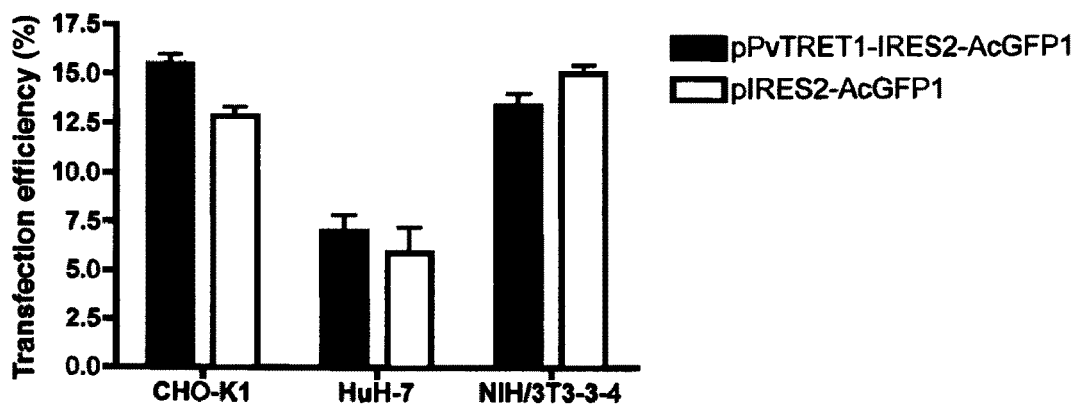
FIG. 6 shows that TRET1 allows mammalian cells to increase trehalose uptake. (A) The transfection efficiency. (B) trehalose uptake of the transfected cells.
Figure 6:
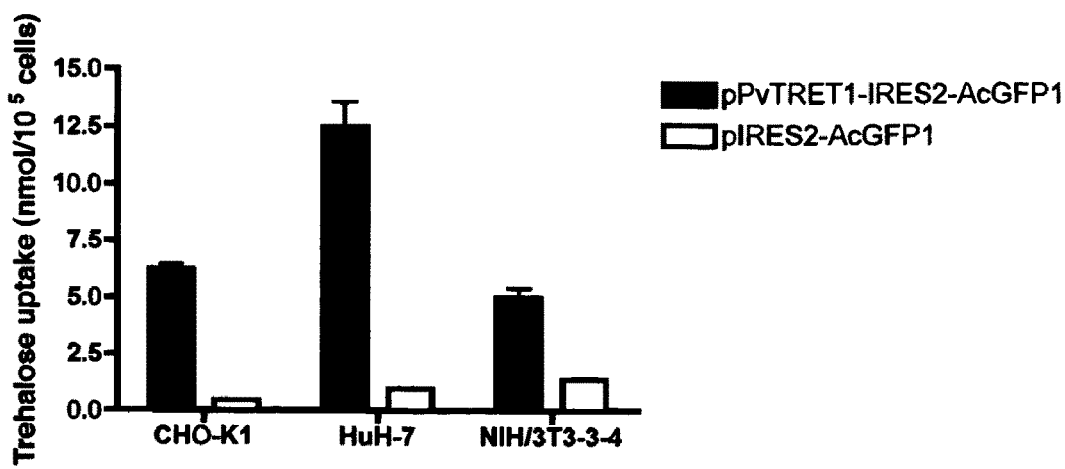

To investigate whether TRET1 has trehalose transport activity, functional assay using with *Xenopus* oocyte expression system was performed. As a result, the translation product of the Tret1 gene actually transported trehalose (FIG. 3A). Of disaccharides, trehalose but not sucrose, maltose and lactose can be transport across the cellular membranes by TRET1 (FIG. 3B). The transport activity was stereochemically specific for trehalose and independent of extracellular pH (between 4.2 and 7.6) and electrochemical membrane potential (FIG. 4). These results indicate that TRET1 is a trehalose-specific facilitated transporter and that the direction of transport is reversible depending on the concentration gradient of trehalose. Indeed, intracellular trehalose could be eliminated when its concentration gradient was reversed between the cytosol and external media (FIG. 5). The extraordinarily high values for apparent Km ($114.5 \pm 27.9$ mM) and Vmax ($7.84 \pm 0.77$ nmol/15 min/oocyte) for trehalose both indicate that TRET1 is a high-capacity transporter of trehalose (FIG. 9), suggesting that TRET1 can retain a high activity for transport even when trehalose concentration is extremely high. In addition, TRET1 was found to function in mammalian cells, suggesting that it confers trehalose permeability on cells regardless of cell types (FIG. 6).

Insects except for *P. vanderplanki* also probably possess transporters like TRET1 because the hemolymph sugar of most insects is trehalose (Wyatt, G. R. (1967) *Adv Insect Physiol* 4, 287-360). By searching in public genome databases such as Flybase, Anobase, KAIKOBLAST, Honey Bee Genome Project, and NCBI BLAST, isolations of Tret1 orthologs form other insects were attempted. As a result, the orthologs were found from the fruit fly (*Drosophila melanogaster*), a malaria mosquito (*Anopheles gambiae*), the European honeybee (*Apis mellifera*) and the silkworm (*Bombyx mori*). In silico, primary structures of deduced proteins of these orthologs showed high similarity to that of TRET1 of *P. vanderplanki*. However, activity of the deduced proteins was unidentified. Thus, the orthologs were isolated from *D. melanogaster, An. gambiae, Ap. mellifera* and *B. mori*, and designated as DmTret1, AgTret1, AmTret1 and BmTret1, respectively (refer to Table 3).

Figure 7:
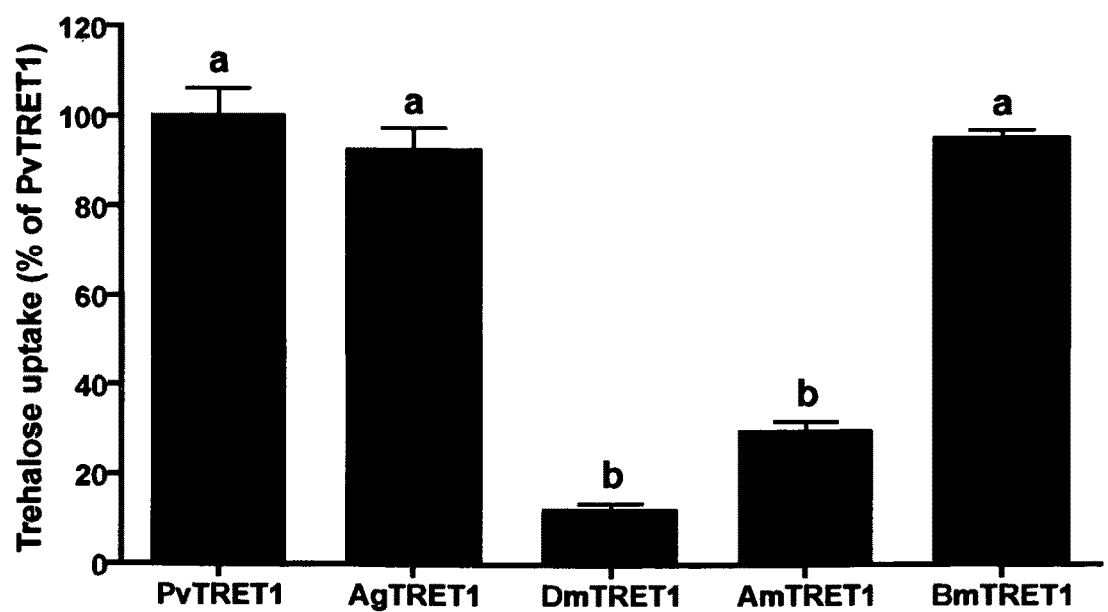
FIG. 7 shows trehalose uptake activity of insect TRET1 derived from *P. vanderplanki*, the fruit fly (*Drosophila melanogaster*), a malaria mosquito (*Anopheles gambiae*), Western honey bee (*Apis mellifera*) and the silkworm (*Bombyx mori*).

Likewise, whether these Tret1-orthologs have trehalose transport activity was examined using the *Xenopus* oocyte expression system. As a result, the oocytes expressing either DmTRET1, AgTRET1, AmTRET1 or BmTRET1 showed trehalose transport activity (FIG. 7), suggesting that Tret1 gene would be widespread in insect taxa.

Figure 8:
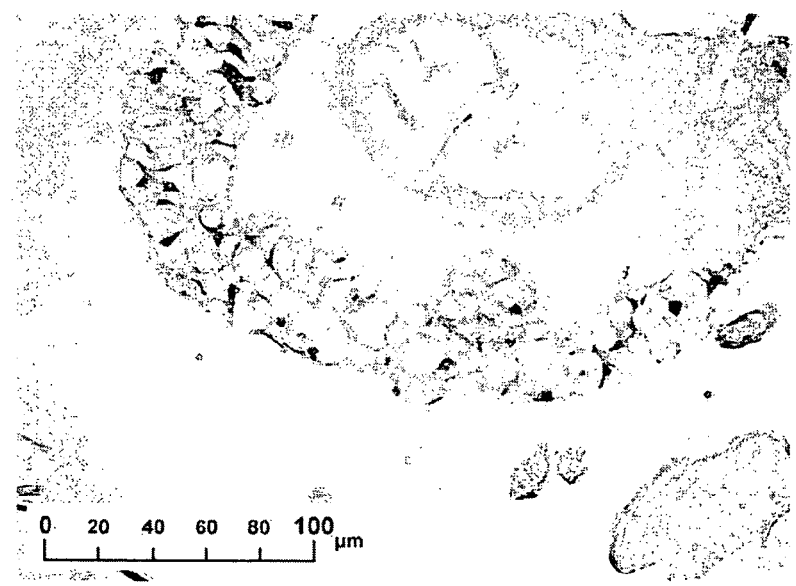
FIG. 8 is a photograph showing that Tret1 gene is expressed mainly in the fat body of larvae of *P. vanderplanki*.
Figure 8:
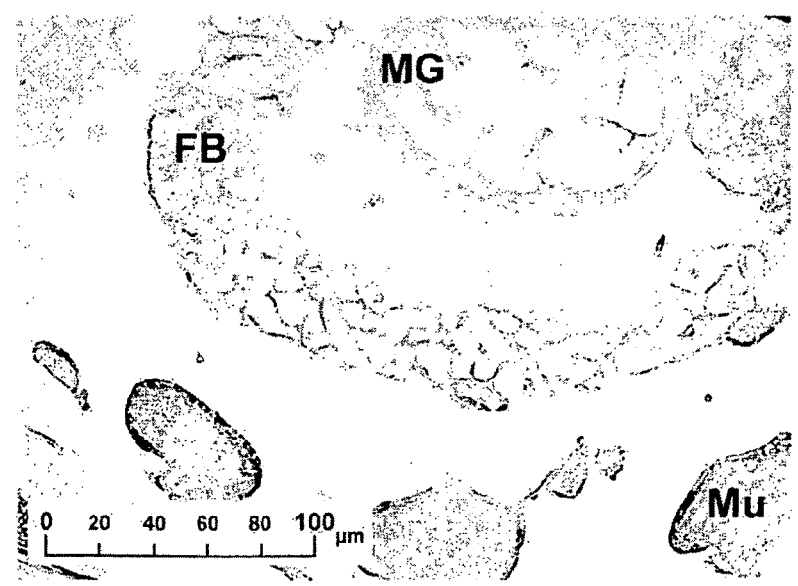

Moreover, to investigate physiological roles of TRET1, in situ hybridization for Tret1 using 24 h desiccated larva of p. vanderplanki. As a result, Tret1 was mainly expressed in the fat body (FIG. 8), indicating that Tret1 is involved in transporting trehalose synthesized in the fat body into hemolymph because the fat body is the organ producing trehalose in insects.

Based on these characteristic features of TRET1, advantages of the present invention will be explained hereinafter.

As shown in table 1, TRET1 derived from insects has several advantages compared with transporters having trehalose uptake activity derived from unicellular organisms. As for MalEFGK$_2$ and MAL11/AGT1 (Boos, W. & Shuman, H. (1998) *Microbiol Mol Biol Rev* 62, 204-229; Stambuk, B. U., et al. (1996) *Eur J Biochem* 237, 876-881; Stambuk, B. U., et al. (1999) *FEMS Microbiol Lett* 170, 105-110; Han, E. K., et al. (1995) *Mol Microbiol* 17, 1093-1107), it is hard to control concentration of intracellular trehalose because direction of transport for both transporters is only inward, and cells require furnishing of ATP when expressing both transporters because both are ATP-dependent transporter. In contrast, as for TRET1, one significant advantage is that very high intracellular trehalose concentrations can be maintained due to this high-capacity transporter. The intracellular trehalose concentration can also be easily controlled by changing the extracellular trehalose concentration without an undesirable influx and/or efflux of other molecules at neutral pH. In addition, since TRET1 is a single gene product, transgenesis into cells should not be difficult.

TABLE 1

| | | | | | | | |
|---|---|---|---|---|---|---|---|
| | | Comparison between TRET1 and other transporters having trehalose uptake activity | | | | | |
| | Origin | Homology to PvTRET1 | Type of transporter | Driving force | Sub-units | Activity at neu-tral pH | Direction of transport | Energy-loss of cells when transporting |
| TRET1 | Insects | — | Passive (facilitated) | Substrate concentration gradient | Homo | + | Inward/outward | − |
| MAL11/Agt1 | Yeasts | 16.7%/87 amino acids | Active | Proton gradient caused by ATP pump | Homo | − | Inward | + |
| MalEGFK$_2$ | Gram-negative bacteria Archaea | 18.5%/119 amino acids | Active | Hydrolysis of ATP | Hetero | ? | Inward | + |

As shown in table 2, introduction of trehalose into cells using expression of Tret1 has several advantages compared with existing techniques for the introduction as well. For example, introduction of bacterial trehalose biosynthetic enzyme genes (otsA and otsB) into human fibroblasts increases intracellular trehalose concentration (Guo, N., et al. (2000) *Nat Biotechnol* 18, 168-171). In this system, these genes are constitutively activated to produce trehalose, so that intracellular carbon sources such as glucose must be consumed. In contrast, when using TRET1, no energy requires for trehalose uptake, so that no intracellular carbon sources would be consumed. Moreover, as for otsA and otsB system, it is hard to eliminate trehalose even when it is no longer necessary. This retention could cause ill effects because trehalose can prevent refolding of denatured-proteins (Singer, M. A. & Lindquist, S. (1998) *Mol Cell* 1, 639-648). In contrast, using TRET1, trehalose is easily and selectively eliminated due to its bidirectional transport. In another approach, engineered switchable pores or extracellular nucleotide-gated channels (engineered α-hemolysin or P2X$_7$ purinergic receptor pore) were created in cellular membranes to allow trehalose uptake (Eroglu, A., et al. (2000) *Nat Biotechnol* 18, 163-167; Elliott, G. D., et al. (2006) *Cryobiology* 52, 114-127). That approach enabled trehalose to move from the extracellular fluid into cells; however, undesired influx and efflux of other molecules probably occur simultaneously. In contrast, TRET1 does not cause the undesired influx and efflux because it possesses strict substrate-selectivity in stereochemistry. Pinocytosis is applicable for incorporation of trehalose into human platelets (Wolkers, W. F., et al. (2001) *Cryobiology* 42, 79-87); however, spontaneous uptake by pinocytosis is largely dependent on cell characteristics so that uptake of a large amount of trehalose is not expected in general use. In contrast, TRET1 confers trehalose permeability on cells regardless of its types once it is expressed in the cells.

nucleotide sequence of SEQ ID NO: 1; (e) a polynucleotide encoding a functionally equivalent protein to a 12-transmembrane protein comprising the amino acid sequence of SEQ ID NO:2 with one or more amino acid substitutions, deletions, additions, and/or insertions in the amino acid sequence of SEQ ID NO: 2; and (f) a polynucleotide encoding a protein comprising amino acid sequence of SEQ ID NO: 11 with one or more amino acid substitutions, deletions, additions, and/or insertions in the amino acid sequence of SEQ ID NO: 2.

Herein, a "functionally equivalent protein" is a protein which confers trehalose permeability on cells, and that forms 12-transmembrane structure.

"12-transmembrane protein" as used herein, refers to a computational prediction for protein structures well known in the art, such as SOSUI (bp.nuap.nagoya-u.ac.jp/sosui/). Herein, 12-transmembrane domains in TRET1 of *P. vanderplanki*, are indicated as SEQ ID NO: 13 (refer to FIG. 10). Therefore, the protein produced from the polynucleotide in

TABLE 2

Comparison among introduction of trehalose into cells

| | Chemical substrate selectivity | Influx of other molecules | Leak of intracellular molecules | Consumption of intracellular carbon sources | Elimination of trehalose when being no longer necessary |
|---|---|---|---|---|---|
| Expression of TRET1 | High (stereochemical selection) | − | − | − | + |
| Utilization of engineered hemolysin or P2X$_7$ | Low (size selection of molecule) | + | + | − | + |
| Expression of bacterial trehalose synthase | High (produce only trehalose) | − | − | + | − |
| Utilization of pinocytosis | Low (unspecific) | + | − | − | − |

Thus, compared with other ways and transporters, using TRET1 predominates as an easy-to-use technique for incorporation of trehalose into cells without any damages.

By establishing a way to introduce trehalose into cells using TRET1, development of cell- and tissue-preservation in dry state would be progressed. In addition, strict substrate specificity of TRET1 may provide major advantages in the screening of newly synthesized trehalose-analogs as a medication for osteoporosis, and polyglutamine and polyalanine disease such as Huntington's disease and oculopharyngeal muscular dystrophy.

Moreover, TRET1 is expected to be a target molecule for insecticides because it is strongly involved in discharging trehalose as a main blood sugar of insects from the fat body into hemolymph.

Therefore, the invention is great of importance to confer several exquisite bioactivities of trehalose on cells.

The present invention relates to trehalose transporter gene and method of introducing trehalose into cells by using the gene. More specifically, the present invention provides a polynucleotide of which encodes a protein having a facilitated trehalose transport activity, wherein the polynucleotide is selected from the group consisting of (a) a polynucleotide encoding a protein comprising the amino acid sequencing of SEQ ID NO: 2; (b) a polynucleotide comprising a coding region of the nucleotide sequence described in SEQ ID NO: 1; (c) a polynucleotide encoding a functionally equivalent protein to a protein comprising the amino acid sequence of SEQ ID NO:2 with one or more amino acid substitutions, deletions, additions, and/or insertions in the amino acid sequence of SEQ ID NO: 2; (d) a polynucleotide that hybridized under highly stringent conditions of 0.2×SSC and 65° C. with a complementary strand of a polynucleotide comprising the the present invention comprises the functionally equivalent protein consisting of any one of amino acid sequences of SEQ ID NO: 13 with one or more amino acid substitutions, deletions, additions, and/or insertions in the amino acid sequence of SEQ ID NO: 2. Herein, nucleotide sequence encoding SEQ ID NO: 13 corresponds to between position 250 and 1572 in SEQ ID NO: 1.

The polynucleotide of the present invention (Tret1) is isolated from *P. vanderplanki*. Nucleotide sequence for Tret1 derived from *P. vanderplanki* is shown in SEQ ID NO: 1. Amino acid sequence for the protein deduced from the Tret1 is shown in SEQ ID NO: 2. Moreover, nucleotide sequence for Tret1 derived from *An. gambiae, D. melanogaster, Ap. mellifera* and *B. mori* are shown in SEQ ID NOs: 3, 5, 7, and 9, respectively. Amino acid sequence for the protein deduced from the Tret1 of *An. gambiae, D. melanogaster, Ap. mellifera* and *B. mori* are shown in SEQ ID NOs: 4, 6, 8, and 10, respectively.

Figure 10:
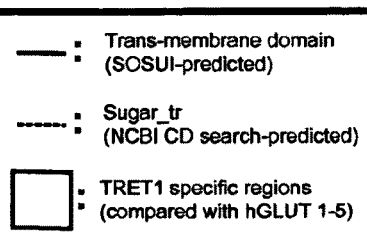
FIG. 10 compares the amino acid sequences of TRET1 and other insect TRET1s. The amino acid sequences of insect TRET1 proteins such as PvTRET1, DmTRET1, AgTRET1, AmTRET1 and BmTRET1 indicate SEQ ID NOs: 2, 4, 6, 8, and 10, respectively.

As shown in FIG. 10, compared between human glucose transporter 1 to 5 (hGLUT1-5) and TRET1 homologs shown in SEQ ID NOs: 2, 4, 6, 8, and 10, Tret1 in insects encodes a protein having characteristic amino acid sequence of SEQ ID NO: 11. Thus, Tret1 in the present invention encodes a protein comprising amino acid sequence of SEQ ID NO: 11 with one or more amino acid substitutions, deletions, additions, and/or insertions in the amino acid sequence of SEQ ID NO: 2. Amino acid sequence of SEQ ID NO: 11 corresponds to the 1$^{st}$ trans-membrane domain in TRET1. In SEQ ID NO: 11, amino acid at position 2, 6, 10, 13, 14, 18, and 20 are any hydrophobic amino acids, and position 7, 11, 15, 17, 26, 27 and 28 are Ser or Ala, Gly or Ala, Val or Ile, Phe or Tyr, Leu or Val, Leu or Val, and Ser or Thr, respectively. In *P. vanderplanki*, amino acid sequence corresponding with SEQ ID NO:

11 is indicated as SEQ ID NO: 12. Therefore, Tret1 in the present invention encodes a protein comprising amino acid sequence of SEQ ID NO: 12 with one or more amino acid substitutions, deletions, additions, and/or insertions in the amino acid sequence of SEQ ID NO: 2. Herein, nucleotide sequences encoding amino acid sequence of SEQ ID NO: 12 corresponds to between position 247 and 333 in nucleotide sequence of SEQ ID NO: 1.

Tret1 of the present invention may be in any form as long as they encode the proteins of the present invention. More specifically, the polynucleotides may be cDNAs synthesized from mRNAs, genomic DNAs, chemically synthesized DNAs or such. Furthermore, polynucleotides with an arbitrary nucleotide sequence based on genetic code degeneracy are encompassed, as long as they encode the proteins of the present invention.

Tret1 of the present invention can be prepared by methods known to those skilled in the art. For example, cDNA libraries are constructed from insect larvae, and hybridization is conducted using DNA segments that encode TRET1 proteins of the present invention as probes, thus preparing DNAs derived from nature. Furthermore, the polynucleotides of the present invention can be produced by preparing RNAs from insect larvae, synthesizing cDNAs using reverse transcriptase, synthesizing oligonucleotide DNAs based on the DNAs encoding the proteins of this invention, and then conducting gene amplification techniques (PCR) (Molecular Cloning edit. Smbrook and Russell. (2001) Publish. Cold Spring Harbor Lab. Press Section 8) using the oligonucleotide DNAs as primers to amplify the cDNAs encoding the proteins of the present invention.

Known methods can be used to isolate mRNAs. For example, total RNA is prepared by guanidine ultracentrifugation (Chirgwin J. M. et al. Biochemistry 18:5294-5299 (1979)), AGPC methods (Chomczynski P. and Sacchi N. Anal. Biochem. 162:156-159 (1987)), and so on, and mRNAs are purified from total RNA using mRNA Purification Kit (GE Healthcare Biosciences) and such. Alternatively, mRNAs can be directly prepared using a QuickPrep mRNA Purification Kit (GE Healthcare Biosciences).

The obtained mRNAs are used to synthesize cDNAs using reverse transcriptase. cDNAs can be synthesized using a kit such as SuperScript First-Strand Synthesis System for RT-PCR (Invitrogen). Alternatively, cDNAs can be synthesized and amplified by the 5'-RACE method (Frohman M. A. et al., Proc. Natl. Acad. Sci. U.S.A. 85: 8998-9002 (1988); Belyavsky A. et al., Nucleic Acids Res. 17: 2919-2932 (1989)) using 5'-Ampli FINDER RACE Kit (Clontech), and PCR.

When using PCR, one can design primers based on portions of the nucleotide sequences of polynucleotides encoding TRET1 proteins of the present invention, then isolate polynucleotide fragments that are highly homologous to these nucleotide sequences or portions thereof, and obtain proteins that are functionally equivalent to the proteins of the present invention based on these fragments.

Hybridization conditions for isolating Tret1 orthologs encoding a protein having trehalose transport activity can be appropriately selected by those skilled in the art. Conditions for hybridization may be stringent conditions. Herein, the phrase "stringent conditions" means conditions in which specific hybrids are formed, while non-specific hybrids are not formed. An embodiment of the stringent conditions of the present invention includes low stringency conditions. Low stringency conditions mean that the washing conditions after hybridization are, for example, 42° C., 5×SSPE, and 0.1% SDS, or preferably 50° C., 5×SSPE, and 0.1% SDS.

Examples of hybridization conditions that are more preferable are highly stringent conditions. An example of highly stringent conditions is 65° C., 0.1×SSPE, and 0.1% SDS. Under such conditions, higher temperatures enable DNAs with higher homology to be obtained more efficiently. However, the combinations of SSPE, SDS, and temperature conditions mentioned above are only examples, and those skilled in the art can appropriately combine the above-mentioned or other factors (for example, probe concentration, probe length, and hybridization reaction time) that determine hybridization stringency to accomplish similar stringencies to those described above.

Proteins encoded by the polynucleotides isolated using such hybridization techniques and gene amplification techniques ordinarily have amino acid sequences with high homology to the TRET1 of the present invention. The present invention encompasses polynucleotides comprising nucleotide sequences with high homology to the nucleotide sequences of SEQ ID NO: 1. Furthermore, the present invention encompasses proteins or peptides comprising amino acid sequences with high homology to the amino acid sequences of SEQ ID NO: 2. As shown in table 3, "High homology" refers to sequence identity of at least 50% or more, preferably 75% or more, and more preferably 85% or more. More preferably, it means an identity of 90% or more, or 95% or more (such as 96% or more, 97% or more, 98% or more, or 99% or more). Identity can be determined using the BLAST algorithm, including BLASTN for nucleic acid sequence and BLASTX for amino acid sequence.

Tret1 orthologs was isolated from *P. vanderplanki; D. melanogaster, An. gambiae, Ap. mellifera* and *B. mori*; so that Tret1 would be widespread in insect taxa. In other words, Tret1 orthologs can be isolated from insects because homologs of Tret1 should exist in other insects. Thus, "insects" as used herein, includes *P. vanderplanki, D. melanogaster, An. gambiae, Ap. mellifera* or *B. mori*; however, it is not to be construed as being limited thereto. Herein, the phrase "homolog of Tret1" means that the gene encoding the protein having that a biological function is equivalent to TRET1 (e.g. trehalose transport activity) in *P. vanderplanki, D. melanogaster, An. gambiae, Ap. mellifera* or *B. mori*.

The homologies of amino acid sequences and nucleotide sequences of the present invention can be determined using the BLAST algorithm according to Karlin and Altschul (Proc. Natl. Acad. Sci. USA 90:5873-5877, 1993). Programs called blastn and blastx have been developed based on this algorithm (Altschul et al. J. Mol. Biol. 215:403-410, 1990). When a nucleotide sequence is analyzed using blastn, based on BLAST, the parameters are set, for example, at score=100 and wordlength=12. Also, when an amino acid sequence is analyzed using blastx, based on BLAST, the parameters are set, for example, at score=50 and wordlength=3. When using the BLAST and Gapped BLAST programs, default parameters for each of the programs are used. Specific procedures for these analysis methods are known.

The polynucleotides encoding a facilitated trehalose transporter, TRET1, of the present invention can be used to confer increase of permeability for trehalose across the cellular membrane to vertebrate cells, insect cells, individual vertebrates, individual insects or plants. More specifically, the present invention provides methods for increase of permeability for trehalose across the cellular membrane to cells, in which the methods comprise expressing TRET1 in the cells. Herein, the phrase "confer increase of permeability for trehalose" means that there is greater trehalose uptake into cells than when TRET1 is not expressed.

To express TRET1 in cells, the polynucleotides encoding the proteins must be introduced into cells. Genes are generally introduced into cells by incorporating the polynucleotides into appropriate vectors. The vectors that are used are not particularly limited, as long as the inserted polynucleotides are stably retained, and the vectors are selected appropriately according to the type of cells to be conferred increase of permeability for trehalose across the cellular membrane. The present invention comprises vectors that comprise these polynucleotides that encode TRET1, and transformed cells that retain these vectors.

Vectors comprising Tret1 of the present invention include plasmid, phage, fosmid or virus. As example of the plasmid, pBluescript (Stratagene), pCR (Invitrogen) can be used. As example of phage, λgt10, λgt11 and EMBL3 can be used. As example of fosmid, pCC1FOS and pCC2FOS (EPICENTRE Biotechnologies) can be used. As example of virus, adenovirus and baculovirus can be used. Moreover, the vectors comprising promoters for effective expression, and a signal sequence for secretion of polypeptide can be used. As example of the promoter, lacZ promoter (Ward et al., Nature (1989) 341, 544-546; FASEB J. (1992) 6, 2422-2427), araB promoter (Better et al., Science (1988) 240, 1041-1043), T7 promoter, SV40 promoter (Mulligan et al., Nature (1979) 277, 108), MMLV-LTR promoter, EF1α promoter (Mizushima et al., Nucleic Acids Res. (1990) 18, 5322), and CMV promoter can preferably be used. As example of the signal sequence, pelB signal sequence (Lei, S. P. et al J. Bacteriol. (1987) 169, 4379) can be used for protein expression in periplasmic space of *E. coli*.

Transformed cells that express TRET1 of the present invention include insect cells, vertebrate cells, yeast or bacteria. Examples of insect cultured cells include Sf9 and Sf21 (both from Invitrogen), and examples of vertebrate cells include NIH/3T3, CHO, HepG2, and Jurkat. The vectors that enable genes to be expressed in these cells include Bac-to-Bac baculovirus expression system (Invitrogen) and the pIZT/V5-His vector (Invitrogen) for insect cultured cells. For vertebrate cells (in particular mammalian cells), pcDNA5/FRT (Invitrogen) or the pGene/V5-His vector of the GeneSwitch system (Invitrogen) can be used for various cells such as NIH/3T3, CHO, HepG2, and Jurkat. For yeast, the pPICZ of the *Pichia* expression system (Invitorgen) can be used for a methylotrophic yeast, *Pichia pastoris*. For bacteria, pET vectors (Novagen) can be used for *Escherichia coli* such as BL21-DE3 (Invitrogen).

Vectors can be introduced into each of the host cells by appropriately using known gene introduction methods, according to the type of host cell. For methods involving transfection, methods such as calcium phosphate coprecipitation, electroporation, and complex formation with DEAE-dextran or with cationic lipids are used. For example, vectors are introduced into insect cultured cells using the cationic lipid for gene introduction, FuGENE HD (Roche). Furthermore, for introduction of vectors into most vertebrate cells (in particular, mammalian cells), the cationic lipid for gene introduction, FuGENE6 (Roche), can be used as described in Example 7. For floating cells such as Jurkat cells, the cationic lipid for gene introduction reagent, DMRIE-C (Invitrogen), may be used.

The present invention also provides an isolated protein encoded by polynucleotide of any one of (a) and (b) hereinafter: (a) a polynucleotide encoding a protein comprising the amino acid sequence of SEQ ID NO: 2, and (b) a polynucleotide comprising a coding region of the nucleotide sequence described in SEQ ID NO: 1.

The protein of the present invention, TRET1, can be synthesized as a recombinant thereof. As example to produce TRET1 derived from *P. vanderplanki*, cDNA library is first prepared (Short, J. M. et al., Nucleic Acid Research, 16, 7583, 1988) from mRNA isolated from Tret1-expressing cells such as cells enucleated from the fat body and cultured cells derived from the fat body, subsequently the gene encoding TRET1 can be isolated form the cDNA library by hybridizing with specific probes designed by being based on nucleotide sequence of SEQ ID NO: 1. TRET1 encoded by polynucleotide thereof can be obtained by methods for protein expression system well known to those skilled in the art. Moreover, the protein of the present invention can be purified from cultured cells expressing TRET1.

The present invention provides a functionally equivalent protein to TRET1 having activity for facilitated transport of trehalose across the cellular membranes. Organisms for isolation of the protein are not restricted, for example, locust, cockroach, and moth being utilized for entomological research can be used.

As examples, the functionally equivalent protein to TRET1 is translated from any one of (c) to (f) hereinafter: (c) a polynucleotide encoding a protein comprising the amino acid sequence of SEQ ID NO:2 with one or more amino acid substitutions, deletions, additions, and/or insertions in the amino acid sequence of SEQ ID NO: 2, (d) a polynucleotide that hybridized under highly stringent conditions with a complementary strand of a polynucleotide comprising the nucleotide sequence of SEQ ID NO: 1, (e) a polynucleotide encoding a 12-transmembrane protein comprising the amino acid sequence of SEQ ID NO:2 with one or more amino acid substitutions, deletions, additions, and/or insertions in the amino acid sequence of SEQ ID NO: 2, and (f) a polynucleotide encoding a protein comprising amino acid sequence of SEQ ID NO: 11 with one or more amino acid substitutions, deletions, additions, and/or insertions in the amino acid sequence of SEQ ID NO: 2.

Herein, 12-transmembrane domains in TRET1 of *P. vanderplanki*, are indicated as SEQ ID NO: 13 (refer to FIG. 10). Therefore, the protein produced from the polynucleotide in the present invention comprises the functionally equivalent protein consisting of any one of amino acid sequences of SEQ ID NO: 27 with one or more amino acid substitutions, deletions, additions, and/or insertions in the amino acid sequence of SEQ ID NO: 2. Herein, nucleotide sequence encoding SEQ ID NO: 13 corresponds to between position 250 and 1572 in SEQ ID NO: 1.

Compared between human glucose transporter 1 (hGLUT1) and TRET1 homologs shown in SEQ ID NOs: 2, 4, 6, 8, and 10, TRET1 in the present invention comprises characteristic amino acid sequence of SEQ ID NO: 11. Thus, Tret1 in the present invention encodes a protein comprising amino acid sequence of SEQ ID NO: 11 with one or more amino acid substitutions, deletions, additions, and/or insertions in the amino acid sequence of SEQ ID NO: 2. Amino acid sequence of SEQ ID NO: 11 corresponds to the 1st trans-membrane domain in TRET1. In SEQ ID NO: 11, amino acid at position 2, 6, 10, 13, 14, 18, and 20 are any hydrophobic amino acids, and position 7, 11, 15, 17, 26, 27 and 28 are Ser or Ala, Gly or Ala, Val or Ile, Phe or Tyr, Leu or Val, Leu or Val, and Ser or Thr, respectively. In *P. vanderplanki*, amino acid sequence corresponding with SEQ ID NO: 11 is indicated as SEQ ID NO: 12. Therefore, Tret1 in the present invention encodes a protein comprising amino acid sequence of SEQ ID NO: 12 with one or more amino acid substitutions, deletions, additions, and/or insertions in the amino acid sequence of SEQ ID NO: 2. Herein, nucleotide sequences encoding amino acid sequence of SEQ ID NO: 12 corresponds to between position 247 and 333 in nucleotide sequence of SEQ ID NO: 1.

Furthermore, the functionally equivalent protein to TRET1 of the present invention comprises an immunologically equivalent protein to TRET1. Herein, "immunologically-equivalent protein to TRET1" refers to a protein cross-reacted with antibodies specifically recognized TRET; however, the antibodies are not particularly limited as long as they are detectable antibodies. For example, immunologically-equivalent protein to TRET1 includes epitope peptides for TRET1, domains of TRET1 comprising the epitopes thereof, and proteins comprising the domains thereof.

In addition, the functionally equivalent protein to TRET1 of the present invention comprises a protein having activity for trehalose transport across the cellular membranes. In other words, the functionally equivalent protein is also defined by biochemical activity thereof. The biochemical activity comprises trehalose transport activity independent of ATP hydrolysis and protein potential, and transport activity for alpha-glucoside except sucrose and maltose.

The functionally equivalent proteins to TRET1 of the present invention can be produced as a fusion protein with other protein and any protein tags. For example, GST, FLAG tag, HA tag and histidine tag may be used for the fusion proteins. The functionally equivalent protein comprises the fusion protein thereof having any one of biochemical function of TRET1, even when the fusion protein possesses a differing activity from TRET1.

The functionally equivalent proteins to TRET1 of the present invention can be isolated by a method well known in the art. For example, highly homologous DNA encoding the functionally equivalent proteins to TRET1 of the present invention may be cloned by screening any DNA library with polynucleotide of SEQ ID NO: 1 as a probe. As example of such DNA library, cDNA library derived from fat body of insects, including *P. vanderplanki, An. gambiae, D. melanogaster, Ap. mellifera* and *B. mori*.

Proteins that are functionally equivalent to TRET1 of the present invention can be prepared by those skilled in the art, for example, by using methods for introducing mutations to amino acid sequences in proteins (such as site-directed mutagenesis (Molecular Cloning edit. Smbrook and Russell. (2001) Publish. Cold Spring Harbor Lab. Press Section 13). Mutations in protein amino acid sequences due to mutations in the nucleotide sequences that encode the proteins may also occur in nature. Polynucleotides encoding such proteins that comprise an amino acid sequence with one or more amino acid substitutions, deletions, or additions to the naturally-occurring TRET1 (SEQ ID NO: 2) are comprised in the polynucleotides of the present invention, as long as they encode proteins functionally equivalent to the naturally occurring proteins. The number of modified amino acids is not particularly limited as long as the modified protein has functions equivalent to TRET1 of the present invention. However, the modified amino acids are generally 50 amino acids or less, preferably 30 amino acids or less, and more preferably 10 amino acids or less (for example, 5 amino acids or less, and 3 amino acids or less).

To retain the function of the protein, the amino acids used for substitution are preferably those comprising similar properties to the original amino acids prior to substitution. Examples of properties of amino acid side chains include: hydrophobic amino acids (A, I, L, M, F, P, W, Y, V), hydrophilic amino acids (R, D, N, C, E, Q, G, H, K, S, T), amino acids comprising the following side chains: aliphatic side-chains (G, A, V, L, I, P); hydroxyl group-containing side-chains (S, T, Y); sulfur atom-containing side-chains (C, M); carboxylic acid- and amide-containing side-chains (D, N, E, Q); base-containing side-chains (R, K, H); and aromatic-containing side-chains (H, F, Y, W) (The letters within parentheses indicate the one-letter amino acid codes).

Proteins functionally equivalent to TRET1 of the present invention can be isolated using hybridization techniques well known to those skilled in the art. More specifically, using the nucleotide sequences of polynucleotides encoding the proteins of the present invention, or portions thereof, those skilled in the art can routinely perform hybridization (Molecular Cloning edit. Smbrook and Russell. (2001) Publish. Cold Spring Harbor Lab. Press Section 14) to isolate DNAs that are highly homologous to these nucleotide sequences, and to obtain functionally equivalent proteins from these DNAs. The present invention also comprises polynucleotides that hybridize under stringent conditions with the polynucleotides encoding TRET1 of the present invention.

Herein, stringent condition refers to the condition described above. The stringency depends on factors such as salt concentration, formamide concentration and temperature for annealing; however, those skilled in the art can appropriately combine the above-mentioned or other factors (for example, probe concentration, probe length, and hybridization reaction time) that determine hybridization stringency to accomplish similar stringencies to those described above.

Using the hybridization technique, DNA encoding proteins functionally equivalent to TRET1 of the present invention can be isolated from insects other than *P. vanderplanki, An. gambiae, D. melanogaster, Ap. mellifera* and *B. mori*. The other insects, for example, are locust, cockroach and moth being utilized in entomological research.

Protein obtained by introducing mutations in TRET1 (SEQ ID NO: 2) and encoded by DNA isolated using the hybridization technique as described above generally shows high homology to the amino acid sequences of SEQ ID NO: 2. As shown in table 3, "High homology" refers to sequence identity of at least 50% or more, preferably 75% or more, and more preferably 85% or more. More preferably, it means an identity of 90% or more, or 95% or more (such as 96% or more, 97% or more, 98% or more, or 99% or more). Identity can be determined using the BLAST algorithm, including BLASTN for nucleic acid sequence, and BLASTX and BLASTP for amino acid sequence on the web site of National Center for Biotechnology Information (NCBI; Altschul, S. F. et al., J. Mol. Biol., 1990, 215(3):403-10; Altschul, S. F. & Gish, W., Meth. Enzymol., 1996, 266:460-480; Altschul, S. F. et al., Nucleic Acids Res., 1997, 25:3389-3402).

On Advanced BLAST 2.1, score (%) for identity of amino acid sequence can be obtained using BLASTP of which parameters are set, for example, at Expect value=10, Gap existence cost=11, Per residue gap cost=1, Lambda ratio=0.86 (default), filter: all OFF, and Matrix: BLOSUM62 (Karlin, S. and S. F. Altschul (1990) *Proc. Natl. Acad. Sci. USA* 87:2264-68; Karlin, S. and S. F. Altschul (1993) Proc. Natl. Acad. Sci. USA 90:5873-7).

TRET1 of the present invention or proteins functionally equivalent to TRET1 of the present invention comprises a protein modified by physiological modification such as glycosylation, labelling with radioisotopes and fluorescent substances, and fusion with other proteins.

TRET1 of the present invention can be obtained as a recombinant protein using any of appropriate gene expression system. To obtain TRET1 of the present invention with genetic engineering, DNA encoding TRET1 of the present invention is transfected into any of appropriate host.

As example of applicable host-vector system for the present invention, pGEX and *E. coli* system can be used. Expression vector, pGEX (GE healthcare bio-science) can be expressed as a fusion protein with glutathione-S-transferase (GST). Thereby, pGEX containing a DNA encoding TRET1 is transfected into *E. coli* strain, BL21, and then induced TRET1-GST fusion protein by adding isopropylthio-β-D-galactoside (IPTG) after several hours. The DNA encoding TRET1 of the present invention, for example, can be obtained by PCR using cDNA library derived from fat body as a template. The GST fusion protein of the present invention can be easily purified using glutathione Sepharose-4B affinity chromatography (Smith, D & Johnson, K. (1988) Gene, 67:31-40).

As host-vector system to obtain recombinant TRET1, the following are applicable. When bacteria are used as the host, expression vectors expressing a fusion protein with histidine tag, HA tag, FLAG tag and so on are available commercially. For yeast, *Pichia* order can be used to produce glycoproteins in common awareness. In terms of glycosylation, baculovirus vector-insect cells system is also available (Luckow et al. Bio/Technology, (1988) 6:47-55). In addition, a method that vectors containing promoters such as CMV, RSV and SV40 are transfected into mammalian cell lines can be used to produce TRET1 of the present invention. Moreover, virus vectors such as retrovirus, adenovirus and adeno-associated virus can also be used for gene introduction into mammalian cell lines.

Furthermore, the present invention provides a method for conferring increase of permeability for trehalose across the cellular membrane to a cell, wherein the method comprises in the cell a protein encoded by the polynucleotide of SEQ ID NO: 1. Moreover, the present invention also provides a method for introduction of trehalose comprising a method for being expressed the gene of the present invention in any of cells. In the present invention, any of cells can be used, and it is not to be construed as being limited thereto. In addition, various methods for gene expression in cells well known in the art can be used to being expressed the gene of the present invention, and it is not to be construed as being limited thereto.

Moreover, the present invention provides a method for introducing trehalose into a cell, wherein the method comprises in the cell a protein encoded by the polynucleotide of SEQ ID NO: 1. Moreover, the present invention also provides a method for introduction of trehalose comprising a method for being expressed the gene of the present invention in any of cells. In the present invention, any of cells can be used, and it is not to be construed as being limited thereto. In addition, various methods for gene expression in cells well known in the art can be used to being expressed the gene of the present invention, and it is not to be construed as being limited thereto.

Therefore, the gene of the present invention (Tret1) appears to be highly useful.

Any patents, published patent applications, and publications sites herein are incorporated by reference.

EXAMPLES

Hereinafter, the present invention will be specifically described using examples; however, it is not to be construed as being limited thereto.

Materials and Methods for Examples

Animal and Cell Culture

*P. vanderplanki* was reared on a milk agar diet under controlled light conditions (13 h light: 11 h dark) at 27° C.

(Kikawada, T., et al. (2005) *Integr Comp Biol* 45, 710-714; Watanabe, M., et al. (2002) *J Exp Biol* 205, 2799-2802). To induce expression of anhydrobiosis-related genes, final instar larvae (each about 1 mg wet body mass) were desiccated by a procedure described in a previous report (Watanabe, M., et al. (2003) *J Exp Biol* 206, 2281-2286).

CHO-K1 (RCB0285), HuH-7 (RCB1366) or NIH3T3-3-4 (RCB1862) cells were provided by the RIKEN Cell Bank (Tsukuba, Japan). CHO-K1 cells were cultured in a Ham's F-12 medium (Sigma-Aldrich) containing 10% fetal bovine serum (FBS) (Tissue Culture Biologicals), 100 U/ml penicillin, 100 μg/ml streptomycin (Sigma-Aldrich) at 37° C., 5% $CO_2$, 95% relative humidity (RH). HuH-7 and NIH3T3-3-4 cells were cultured in DMEM (Sigma-Aldrich) supplemented with 10% FBS, 100 U/ml penicillin, 100 μg/ml streptomycin (Sigma-Aldrich) at 37° C., 5% CO2, 95% RH.

Tret1 cDNA Cloning from *P. vanderplanki, D. melanogaster, An. gambiae, Ap. mellifera* and *B. mori*

In Pv-EST database (Kikawada, T., et al. (2006) *Biochem Biophys Res Commun* 348, 56-61), 6 EST clones annotated as sugar transporter-like genes were assembled into one cluster designated as Tret1 (FIG. 1). The full-length Tret1 cDNA was obtained by 5'- and 3'-RACE using a SMART RACE cDNA Amplification kit (Clontech).

The full-length Tret1 cDNA was subcloned into pCR4Blunt-TOPO (Invitrogen, Tokyo, Japan) to produce pCR-TRET1. DNA sequences were analyzed with GENE-TYX-MAC (Genetyx Co.). Motif analysis was performed with Pfam and secondary structures of membrane proteins were predicted using the SOSUI system. For isolation of Tret1 orthologs from *D. melanogaster, An. gambiae, Ap. mellifera* and *B. mori*, public genome databases such as Flybase, Anobase, KAIKOBLAST, BeeBase, and NCBI BLAST were searched with tBlastn. These cDNA clones were cloned by PCR using primers designed by results of DNA database search, and designated as DmTret1, AgTret1, AmTret1 and BmTret1.

Northern Blot Analysis

Total RNA from the larvae either undergoing dehydration or submerged in 1% (w/v) NaCl was isolated with TRizol (Invitrogen). Fifteen μg of total RNA was run on a 1% agarose-20 mM guanidine isothiocyanate gel, and transferred onto Hybond N-Plus membrane (GE Healthcare Bio-Science, Tokyo, Japan). Hybridization was carried out at 42° C. in 5×SSPE containing 0.5% SDS and 50% formamide. For hybridization probes, full-length Tret1 cDNA fragments were synthesized from pCR-TRET1 by PCR and labeled with $\alpha$-$^{32}$P-dATP using Strip-Ez labeling kit (Ambion). The membranes were analyzed by BAS 2500 (Fuji Film).

Western Blot Analysis

Proteins were extracted from larvae as for Northern blot analysis with a 20-fold volume of tissue-protein extraction reagent (T-PER; Pierce) containing a protease inhibitor cocktail (Complete; Roche Diagnostics). A 7.5 μg protein sample was subjected to SDS-PAGE using 5-20% gradient gels and subsequently transferred onto Hybond-P membranes (GE Healthcare Bio-Science). Membranes were treated with anti-PvTRET1-1 polyclonal antibody, and then goat anti-Rabbit IgG (H+L) conjugated with horseradish peroxidase (American Qualex). Anti-PvTRET1-1 antibody was raised in a rabbit against the synthesized peptide corresponding to the TRET1 sequence at positions 242-254 (LRGKKADVEPELK) and purified by affinity-chromatography using the peptide (Sigma-Aldrich-Japan). Immunoreacted proteins were detected with Immobilon™ Western Chemiluminescent HRP Substrate (Millipore) and analyzed by LAS-3000 (Fuji Film).

In Situ Hybridization (ISH)

ISH was performed under contract with Genostaff (Tokyo, Japan). A larva of *P. vanderplanki* dehydrated for 24 h was fixed with Tissue Fixative (Genostaff), then embedded in paraffin by their proprietary procedures, and sectioned at 6 μm. The tissue sections were de-waxed with xylene, and rehydrated through an ethanol series and PBS, fixed in 4% paraformaldehyde in PBS for 15 min, and then treated with 15 μg/ml Proteinase K in PBS for 30 min at 37° C. After washing with PBS, the sections were refixed with 4% paraformaldehyde in PBS, placed in 0.2M HCl for 10 min, acetylated by incubation in 0.1M triethanolamine-HCl, pH8.0, 0.25% acetic anhydride for 10 min, and dehydrated through a series of ethanol solutions. Probe for a 525 bp cDNA fragment was designated from position 300 to 824 of Tret1 cDNA, and labeled with digoxygenin (DIG) RNA Labeling Kit (Roche Diagnostics, Tokyo, Japan). Hybridization was performed with the probe at a concentration of 100 ng/ml in the Probe Diluent (Genostaff) at 60° C. for 16 h. After hybridization, the sections were washed in 5× HybriWash (Genostaff), equal to 5×SSC, at 60° C. for 20 min and then in 50% formamide, 2× HybriWash at 60° C. for 20 min, followed by RNase treatment in 50 μg/ml RNaseA in 10 mM Tris-Cl, pH8.0, 1M NaCl and 1 mM EDTA. Then the sections were washed twice with 2× HybriWash at 60° C. for 20 min, twice with 0.2× HybriWash at 60° C. for 20 min, and once with TBS-T (0.1% Tween20 in TBS). After treatment with 0.5% blocking reagent (Roche Diagnostics) in TBS-T for 30 min, the sections were incubated with anti-DIG AP conjugate (Roche Diagnostics) diluted 1:1000 with TBS-T for 2 h. The sections were washed twice with TBS-T and then incubated in 100 mM NaCl, 50 mM $MgCl_2$, 0.1% Tween20 and 100 mM Tris-Cl (pH 9.5). Coloring reactions were performed with BM purple AP substrate (Roche Diagnostics) overnight and then washed with PBS. The sections were counterstained with Kernechtrot stain solution (Muto Pure Chemicals) and mounted with Malinol (Muto Pure Chemicals).

Tret1 cRNA Synthesis

The capped RNA (cRNA) expression vector pTRET1-XbG-ev1 series was constructed as follows: ORF of either Tret1, DmTret1, AmTret1, AgTret1 or BmTret1 cDNA was amplified with PCR using specific primers containing Bgl II site at the 5'-end on each primer, respectively. The PCR products were digested with the restriction enzymes, and cloned into the site of Bgl II in pXbG-ev1 (Preston, G. M., et al. (1992) *Science* 256, 385-387). ORF of hGLUT1 cDNA was obtained by digestion of pSPMM1 with BamH I, and then subcloned into the site of Bgl II in pXbG-2. Template DNAs for cRNA synthesis were amplified from the corresponding cRNA expression vectors with a high fidelity DNA polymerase, KOD—Plus—, (TOYOBO). The cRNAs were synthesized with mMESSAGE mMACHINE T7 Kit (Ambion), and then purified with RNeasy MiniElute Cleanup kit (Qiagen).

Expression of TRET1 in *Xenopus* Oocytes

Stage V or VI oocytes were extirpated from *X. laevis* females, and digested ovarian lobes with 0.2% (w/v) collagenase, type II (Sigma-Aldrich) in $Ca^{2+}$-free modified Barth's saline (MBS; 88.0 mM NaCl, 1.0 mM KCl, 2.4 mM $NaHCO_3$, 15.0 mM Tris-Cl, 0.82 mM $MgSO_4$, 10 μg/μl penicillin and streptomycin, pH7.6) at 15° C. for 3 h. The oocytes were microinjected with 40 nl of either 1 ng/nl of the TRET1::AcGFP1 or AcGFP1 cRNA, or nuclease-free water (Invitrogen) as a negative control. In order to express TRET1, the oocytes were incubated in MBS (containing 0.41 mM $CaCl_2$) for 3-4 days after injection at 15° C. Fluorescence images of the oocytes injected with the cRNA were observed and analyzed with a fluorescence microscope BZ-8000 (KEYENCE).

Functional Zero-Trans Assay of TRET1 in *Xenopus* Oocyte

All uptake assays for zero-trans trehalose and/or other sugars were performed using *Xenopus* oocytes expressing TRET1 at 15° C. in MBS containing appropriate concentrations of sugars. Sugar concentrations were determined using HPLC (Watanabe, M., et al. (2002) *J Exp Biol* 205, 2799-2802). All assays were carried out in triplicate. No degradation of the sugars used in this study was detected in *Xenopus* oocytes extracts when incubated for 3 h at 37° C. (data not shown).

Functional Assay of TRET1 in Mammalian Cells

The TRET1 expression vector, pPvTRET1-IRES2-AcGFP1, was constructed as follows: ORF of Tret1 was obtained by digestion of pXbG-PvTRET1 with EcoR I and Bgl II and subcloned into the Bgl II/EcoR I site in pIRES2-AcGFP1 vector (Clontech). The cells were seeded on 35 mm culture dishes (Falcon® 1008, Becton Dickinson) at $2×10^5/2$ ml of medium/dish, incubated for 24 h, and transfected with pPvTRET1-IRES2-AcGFP1 using FuGene6 (Roche Diagnostics) according to the instruction manual. Control cells were transfected with the vector alone (pIRES2-AcGFP1). Two days after transfection, fresh medium containing 100 mM trehalose was added. After incubation for 3 h, the cells were rinsed with ice-cold D-PBS (Sigma-Aldrich) three times, harvested, and trehalose was measured in the cells. All assays were carried out in triplicate. No degradation of trehalose was detected in extracts of these cells when incubated for 3 h at 37° C. (data not shown). To examine transfection efficiency, we counted cells expressing AcGFP1 with a flow cytometer (EPICS ELITE; Beckman Coulter).

Statistical Analysis

Results are reported as means±SEM. Statistical differences were evaluated with Tukey's multiple comparison tests following one-way analysis of variance (ANOVA) (Prism version 4; GraphPad Software).

Example 1

Molecular Cloning of Tret1 and Predicted Structure of TRET1

Trehalose is the major hemolymph sugar in most insects. It is predominantly synthesized in the fat body and released into the hemolymph (Wyatt, G. R. (1967) *Adv Insect Physiol* 4, 287-360). Although 44 homologues containing a sugar transporter motif exist in *Drosophila melanogaster* according to the protein family database, thus far no trehalose transporter has been identified because it is not possible to estimate the substrate specificity from the primary structure alone.

Larvae of the sleeping chironomid, *Polypedilum vanderplanki*, a temporary rock pool dweller, undergo complete dehydration during dry periods followed by rehydration and resumption of activity when moisture is available. This biological state of tolerance to extreme desiccation is referred to as "cryptobiosis" or "anhydrobiosis" (Keilin, D. (1959) *Proc R Soc London* (B) 150, 149-191). During desiccation or salt stress larvae accumulate up to 20% of their dry mass as trehalose (Watanabe, M., et al. (2002) *J Exp Biol* 205, 2799-2802; Watanabe, M., et al. (2003) *J Exp Biol* 206, 2281-2286;

Kikawada, T., et al. (2005) *Integr Comp Biol* 45, 710-714). These observations indicate strongly that trehalose transporter genes must be highly expressed in the fat body and that it should be feasible to isolate trehalose transporter genes from *P. vanderplanki* larvae.

Thus, candidates for trehalose transporter genes were identified in our original *P. vanderplanki* EST (Pv-EST) database using total RNA from larvae desiccated for 0, 12 or 36 h. The inventors then identified a subset of six EST clones (PD1202M17f, PD3608G15f, PD3606D10f, PS1205C05f, PD1204L14f and PD1202F04f) that form a single cluster annotated as a sugar transporter (FIG. 1A). Based on these data, and followed by 5'- and 3'-RACE, we obtained full-length cDNA (~2.3 kb) designated as Tret1 of which a single open reading frame (ORF) encodes a 55-kDa protein of 504 amino acids (FIG. 1A). TRET1 has a domain for sugar (and other) transport (Pfam accession number: PF00083) located at amino acid residues 46 and 484 (FIG. 1B) for which the E-value was 2.8e-97. The family of sugar (and other) transporters contains the GLUT/SLC2A family, and belongs to the Major Facilitator Superfamily (MFS). From the prediction of secondary structure of membrane proteins using SOSUI analysis, TRET1 is thought to form a 12-transmembrane structure (FIG. 1C) which is typical for the MFS. An additional site for N-linked glycosylation is located in the $1^{st}$ loop at position 73 of TRET1 (FIG. 1C), suggesting that the loop is extracellular. The prediction of protein localization sites in cells using PSORT II (psort.ims.u-tokyo.ac.jp/) predicted that TRET1 is localized in the cellular membrane with probability 87.0%. These results suggest that TRET1 would be a membrane protein having an activity to facilitate transport of any sugar(s) across the cellular membranes.

Example 2

Gene Expression pattern of Tret1 is Consistent with Pattern of Trehalose Accumulation in *P. vanderplanki*

Northern blot analyses showed that both accumulation of mRNA for TRET1 were increased by desiccation (FIG. 2). Total RNA was isolated from the larvae at various times during desiccation. Northern blot analyses were performed using the full-length TRET1 cDNA as a probe which revealed a single 2.3 kb transcript. This expression pattern is in accordance with the known pattern of trehalose accumulation in these larvae (Watanabe, M., et al. (2002) *J Exp Biol* 205, 2799-2802; Watanabe, M., et al. (2003) *J Exp Biol* 206, 2281-2286). Thus, TRET1 would be the sugar transporter involved in trehalose metabolism.

Example 3

TRET1 is a Trehalose-Specific Transporter

Functional expression of TRET1 in *Xenopus* oocytes showed that uptake of trehalose into oocytes expressing TRET1 increased linearly for at least 6 h when incubated in 105 mM trehalose (FIG. 3A). *Xenopus* oocytes expressing either TRET1 or hGLUT1 were incubated in 105 mM of various sugars for 3 h. Tre: trehalose; Mal: maltose; Suc: sucrose; Lac: lactose; MAG: methyl-a-glucopyranoside; and 2-DOG: 2-deoxy-glucose (FIG. 3B). The recognition of substrate was highly specific. Maltose, sucrose and lactose (4-O-b-D-galactopyranosyl-D-glucose, Gal(b1-4)Glc) were not transported and methyl-a-glucoside (MAG) and 2-deoxyglucose (2-DOG) were transported at a much lower rate (FIG. 3B left). For comparison, the Glut1 (TC: 2.A.1.1.28) gene product transported only 2-DOG (FIG. 3B right). These results indicate that TRET1 is a trehalose-specific transporter unlike well-known glucose transporter such as hGLUT1.

Example 4

TRET1 is a Facilitated Transporter

In General, transporters contain two sub-classes: facilitated transporters and secondary active transporters. Activities of secondary active transporters are dependent on the electrochemical membrane potential resulting from the distribution of ions such as $H^+$. For example, proton-dependent MAL11/AGT1 can act only under acidic extracellular conditions (Stambuk, B. U., et al. (1996) *Eur J Biochem* 237, 876-881). On the other hand, facilitated transporters function independently of the electrochemical membrane potential. *Xenopus* oocytes expressing TRET1 were incubated in 105 mM trehalose at pH 4.2 and 7.6 for 3 h. As a result, TRET1 acted over a wide extracellular pH range, between 4.2 and 7.6 (FIG. 4A).

*Xenopus* oocytes expressing TRET1 were incubated in 105 mM trehalose with either control buffer (Mock; 0.1% acetone), or buffer containing various concentrations of nigericin ($Na^+$, $K^+$-ionophore), valinomycin ($K^+$-ionophore) or CCCP ($H^+$-ionophore, uncoupler) for 3 h. As a result, reduction of the electrochemical membrane potential and ATP synthesis caused by ionophores such as valinomycin ($K^+$-ionophore) and nigericin ($Na^+$, $K^+$-ionophore), and an uncoupler such as carbonylcyanide m-chlorophenylhydrazone (CCCP; $H^+$-ionophore) did not significantly affect the transport activity of TRET1 (FIG. 4B). These properties indicate that TRET1 is a facilitated transporter.

Example 5

TRET1 can Transport Trehalose Bi-Directionally

In general, facilitated transporters enable their substrates to flow across membranes down concentration gradients. *Xenopus* oocytes expressing TRET1 were first incubated in 105 mM trehalose for 3 h, and then transferred into trehalose-free buffer and trehalose content was examined over time. As a result, the transport of trehalose was shifted from an inward to outward direction when its concentration gradient was reversed between the cytosol and external media (FIG. 5). This characteristic feature enables cells to easily discharge excess trehalose by reducing its concentration in the extracellular environment.

Example 6

TRET1 Acts Independently of Cell Type

Either TRET1 expression vector (pPvTRET1-IRES2-AcGFP1) or vector only (pIRES2-AcGFP1) was transfected into mouse fibroblasts (NIH/3T3), Chinese hamster ovary cells (CHO-K1), or human hepatoma cells (HuH-7). The transfection efficiency was estimated from the ratio of AcGFP1-expressing cells analyzed by a flow cytometer (FIG. 6A). The transfected cells were incubated in medium containing 100 mM trehalose for 3 h to determine trehalose uptake. In all of these Tret1-transfected lines, trehalose uptake was significantly increased 4- to 14-fold higher than those transfected with vector alone (FIG. 6B). Taken with the results on expression in *Xenopus* oocytes, these data show that TRET1 confers trehalose permeability in cells from other vertebrates, including mammals.

Example 7

TRET1 is Widespread in Insects

Insects except for *P. vanderplanki* also probably possess transporters like TRET1 because the hemolymph sugar of most insects is trehalose (Wyatt, G. R. (1967) *Adv Insect Physiol* 4, 287-360). By searching in public genome databases such as Flybase (flybase.bio.indiana.edu/), Anobase (www.anobase.org), KAIKOBLAST (kaikoblast.dna.affrc.go.jp/), Honey Bee Genome Project (www.hgsc.bcm.tmc.edu/projects/honeybee/), and NCBI BLAST (www.ncbi.nlm.nih.gov/blast/Blast.cgi), Tret1 orthologs form other insects were found. Based on data for the obtained nucleotide sequences, PCR was carried out to obtain cDNA encoding TRET1 homolog. As a result, the orthologs were found from the fruit fly (*Drosophila melanogaster*), a malaria mosquito (*Anopheles gambiae*), the European honeybee (*Apis mellifera*) and the silkworm (*Bombyx mori*). In silico, primary structures of deduced proteins of these orthologs showed high similarity to that of TRET1 of *P. vanderplanki*. However, activity of the deduced proteins was unidentified. Thus, the orthologs were isolated from *D. melanogaster*, *An. gambiae*, *Ap. mellifera* and *B. mori*, and designated as DmTret1, AgTret1, AmTret1 and BmTret1, respectively. Proteins encoding these Tret1-ortologs showed high homology to TRET1 of *P. vanderplanki* (Table 3).

Likewise, whether these Tret1-orthologs have trehalose transport activity was examined using the *Xenopus* oocyte expression system incubated in 105 mM of trehalose for 3 h. As a result, the oocytes expressing either DmTRET1, AgTRET1, AmTRET1 or BmTRET1 showed trehalose transport activity with interspecies difference (FIG. 7), suggesting that Tret1 gene would be widespread in insect taxa.

TABLE 3

Homology of amino acid sequence among TRET1 homologs

|  | AgTRET1 | DmTRET1 | AmTRET1 | BmTRET1 |
| --- | --- | --- | --- | --- |
| PvTRET1 | 80.4%/<br>504 aa | 76.0%/<br>501 aa | 58.7%/<br>489 aa | 58.5%/<br>504 aa |

TABLE 3-continued

Homology of amino acid sequence among TRET1 homologs

|  | AgTRET1 | DmTRET1 | AmTRET1 | BmTRET1 |
| --- | --- | --- | --- | --- |
| AgTRET1 |  | 80.4%/<br>504 aa | 59.2%/<br>503 aa | 59.9%/<br>504 aa |
| DmTRET1 |  |  | 62.1%/<br>462 aa | 56.5%/<br>504 aa |
| AmTRET1 |  |  |  | 55.1%/<br>486 aa |

Example 8

TRET1 is Involved in Discharging Trehalose from the Fat Body

In situ hybridization was carried out using either anti-sense (FIG. 8 upper) or sense (FIG. 8 lower) ribo-probes for Tret1 mRNA to hybridize to cross-sections of a dehydrating larvae in the thorax of *P. vanderplanki* en route to anhydrobiosis after 24 h of dehydration. Magnifications were x400. FB: fat body; Mg: midgut; Mu: muscle. Tret1 was mainly expressed in the fat body and not in other tissues including the midgut, muscle and integuments after 24 h of dehydration. In insects, trehalose in the hemolymph is synthesized in the fat body (Wyatt, G. R. (1967) *Adv Insect Physiol* 4, 287-360). This result suggests that the Tret1 gene is involved in transporting trehalose synthesized in the fat body into the hemolymph.

Example 9

TRET1 is a High-Capacity Transporter

Figure 9:
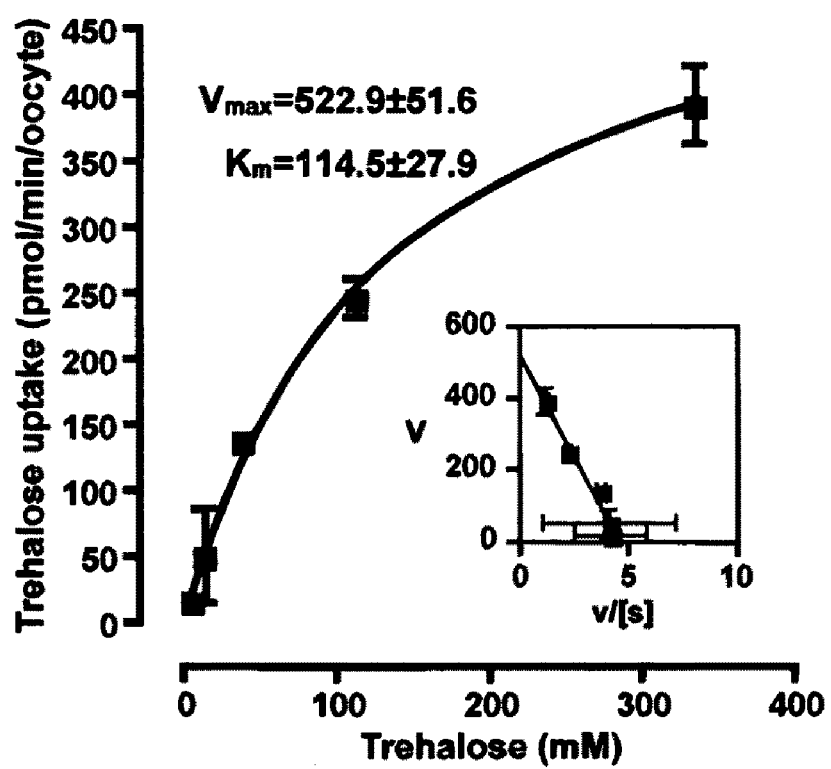
FIG. 9 shows kinetics analysis of zero-trans activity of TRET1 for trehalose.

*Xenopus* oocytes expressing TRET1 were incubated in various concentrations of trehalose for 15 min. Uptake data were fitted to the Michaelis-Menten and Eadie-Hofstee (inset of FIG. 9) equations. Such kinetic analyses showed that apparent Km and Vmax values of TRET1 activity for trehalose were 114.5±27.9 mM and 522.9±51.6 µmol/min/oocyte, respectively (FIG. 9). This Km is exceptionally high and shows a low-affinity for substrate compared to typical sugar transporters such as GLUT1 (~3 mM of glucose), GLUT2 (~17 mM of glucose), and GLUT4 (~6.6 mM of glucose) (Uldry, M., et al. (2002) *FEBS Lett* 524, 199-203). The Vmax for TRET1 was considerably higher, indicating that TRET1 is a high-capacity trehalose transporter.

What is claimed is:

1. A method of increasing permeability of trehalose through a cellular membrane of an isolated cell, comprising the steps of,
isolating a polynucleotide selected from the group consisting of a polynucleotide encoding a protein comprising the amino acid sequence of SEQ ID NO: 2 and a polynucleotide comprising the nucleotide sequence of SEQ ID NO: 1;
transforming an isolated cell with the polynucleotide; and
culturing the isolated cell transformed with the polynucleotide and producing a protein comprising the amino acid sequence of SEQ ID NO: 2 to thereby increase of trehalose through the cellular membrane of the isolated cell.

\* \* \* \* \*

SEQUENCE LISTING

```
<160> NUMBER OF SEQ ID NOS: 13

<210> SEQ ID NO 1
<211> LENGTH: 2337
<212> TYPE: DNA
<213> ORGANISM: Polypedilum vanderplanki
<220> FEATURE:
<221> NAME/KEY: CDS
```

<222> LOCATION: (121)..(1635)

<400> SEQUENCE: 1

```
gacttgaagg acttggattc gtcaagtgac gaagaagaag atcttcaaaa aaatcgcaag    60
caatttcaac aagcaaaatc agccagtggt gcatccaaaa agtctattag tttctttgac   120
```

| | | | | | | | | | | | | | | | | |
|---|---|---|---|---|---|---|---|---|---|---|---|---|---|---|---|---|
| atg | gaa | ctc | aat | aat | aaa | gaa | gat | agt | cca | cgt | cat | acc | gta | cct | ttt | 168 |
| Met | Glu | Leu | Asn | Asn | Lys | Glu | Asp | Ser | Pro | Arg | His | Thr | Val | Pro | Phe | |
| 1 | | | | 5 | | | | | 10 | | | | | 15 | | |
| gta | cgt | caa | att | act | gaa | gat | gga | aaa | gca | aaa | ttg | gaa | att | tat | cga | 216 |
| Val | Arg | Gln | Ile | Thr | Glu | Asp | Gly | Lys | Ala | Lys | Leu | Glu | Ile | Tyr | Arg | |
| | | | | 20 | | | | | 25 | | | | | 30 | | |
| ccc | act | aca | aat | cca | att | tat | att | tat | act | cag | ata | ttg | gca | gca | att | 264 |
| Pro | Thr | Thr | Asn | Pro | Ile | Tyr | Ile | Tyr | Thr | Gln | Ile | Leu | Ala | Ala | Ile | |
| | | 35 | | | | | 40 | | | | | 45 | | | | |
| gca | gtc | tca | atg | ggt | tca | atg | gta | gtt | gga | ttt | gca | tct | gcc | tac | acc | 312 |
| Ala | Val | Ser | Met | Gly | Ser | Met | Val | Val | Gly | Phe | Ala | Ser | Ala | Tyr | Thr | |
| | 50 | | | | | 55 | | | | | 60 | | | | | |
| tca | cct | gca | tta | gta | tca | atg | cag | aat | aca | aca | atc | aca | tct | ttt | aaa | 360 |
| Ser | Pro | Ala | Leu | Val | Ser | Met | Gln | Asn | Thr | Thr | Ile | Thr | Ser | Phe | Lys | |
| 65 | | | | | 70 | | | | | 75 | | | | | 80 | |
| gtg | aca | gaa | caa | gaa | gca | agc | tgg | gta | gga | gga | atc | atg | cca | ctt | gcc | 408 |
| Val | Thr | Glu | Gln | Glu | Ala | Ser | Trp | Val | Gly | Gly | Ile | Met | Pro | Leu | Ala | |
| | | | | 85 | | | | | 90 | | | | | 95 | | |
| ggt | tta | gcc | ggt | ggt | att | gct | ggt | gga | cca | ttt | att | gaa | tat | ttg | ggc | 456 |
| Gly | Leu | Ala | Gly | Gly | Ile | Ala | Gly | Gly | Pro | Phe | Ile | Glu | Tyr | Leu | Gly | |
| | | | 100 | | | | | 105 | | | | | 110 | | | |
| aga | aaa | aat | aca | att | ttg | gcc | aca | gca | gtt | ccc | ttt | att | gtt | gcc | tgg | 504 |
| Arg | Lys | Asn | Thr | Ile | Leu | Ala | Thr | Ala | Val | Pro | Phe | Ile | Val | Ala | Trp | |
| | | 115 | | | | | 120 | | | | | 125 | | | | |
| ctt | cta | atc | gcc | ttt | gcg | aac | tct | att | tgg | atg | gtg | tta | gca | gga | cgt | 552 |
| Leu | Leu | Ile | Ala | Phe | Ala | Asn | Ser | Ile | Trp | Met | Val | Leu | Ala | Gly | Arg | |
| | 130 | | | | | 135 | | | | | 140 | | | | | |
| gct | tta | tca | gga | ttt | tgt | gtc | ggt | att | gct | tca | ctt | tca | ttg | cct | gtt | 600 |
| Ala | Leu | Ser | Gly | Phe | Cys | Val | Gly | Ile | Ala | Ser | Leu | Ser | Leu | Pro | Val | |
| 145 | | | | | 150 | | | | | 155 | | | | | 160 | |
| tac | tta | ggt | gaa | aca | gtt | caa | ccg | gaa | gtt | cgt | ggc | aca | ctt | ggt | tta | 648 |
| Tyr | Leu | Gly | Glu | Thr | Val | Gln | Pro | Glu | Val | Arg | Gly | Thr | Leu | Gly | Leu | |
| | | | | 165 | | | | | 170 | | | | | 175 | | |
| tta | cca | aca | gct | ttt | ggt | aat | atc | ggt | ata | tta | ata | tgt | ttt | gtg | gct | 696 |
| Leu | Pro | Thr | Ala | Phe | Gly | Asn | Ile | Gly | Ile | Leu | Ile | Cys | Phe | Val | Ala | |
| | | | 180 | | | | | 185 | | | | | 190 | | | |
| gga | aaa | tat | gtg | aat | tgg | tca | ggt | cta | gct | ttc | atc | ggt | agt | att | ttg | 744 |
| Gly | Lys | Tyr | Val | Asn | Trp | Ser | Gly | Leu | Ala | Phe | Ile | Gly | Ser | Ile | Leu | |
| | | 195 | | | | | 200 | | | | | 205 | | | | |
| ccg | att | cca | ttt | atg | gtt | tta | aca | tta | ttg | att | ccc | gag | aca | cct | aga | 792 |
| Pro | Ile | Pro | Phe | Met | Val | Leu | Thr | Leu | Leu | Ile | Pro | Glu | Thr | Pro | Arg | |
| | 210 | | | | | 215 | | | | | 220 | | | | | |
| tgg | ttt | gtg | aca | cgt | ggt | cgt | gaa | gaa | aga | gca | aga | aaa | gca | tta | caa | 840 |
| Trp | Phe | Val | Thr | Arg | Gly | Arg | Glu | Glu | Arg | Ala | Arg | Lys | Ala | Leu | Gln | |
| 225 | | | | | 230 | | | | | 235 | | | | | 240 | |
| tgg | cta | aga | gga | aag | aaa | gct | gat | gtt | gaa | cct | gaa | ctt | aag | gga | ata | 888 |
| Trp | Leu | Arg | Gly | Lys | Lys | Ala | Asp | Val | Glu | Pro | Glu | Leu | Lys | Gly | Ile | |
| | | | | 245 | | | | | 250 | | | | | 255 | | |
| gtg | aaa | tct | cat | tgt | gaa | gct | gaa | cgt | cat | gca | tca | caa | aat | gct | att | 936 |
| Val | Lys | Ser | His | Cys | Glu | Ala | Glu | Arg | His | Ala | Ser | Gln | Asn | Ala | Ile | |
| | | | 260 | | | | | 265 | | | | | 270 | | | |
| ttt | gat | cta | atg | aaa | cga | agc | aac | tta | aaa | cca | tta | ttg | att | gct | ctc | 984 |
| Phe | Asp | Leu | Met | Lys | Arg | Ser | Asn | Leu | Lys | Pro | Leu | Leu | Ile | Ala | Leu | |
| | | 275 | | | | | 280 | | | | | 285 | | | | |

|     |     |     |     |     |     |     |     |     |     |     |     |     |     |     |     |       |
|-----|-----|-----|-----|-----|-----|-----|-----|-----|-----|-----|-----|-----|-----|-----|-----|-------|
| gga | ctg | atg | ttc | ttc | caa | caa | ttg | tcc | ggt | atc | aat | gct | gtc | att | ttc | 1032  |
| Gly | Leu | Met | Phe | Phe | Gln | Gln | Leu | Ser | Gly | Ile | Asn | Ala | Val | Ile | Phe |       |
|     | 290 |     |     |     |     | 295 |     |     |     |     | 300 |     |     |     |     |       |
| tat | aca | gtg | tca | ata | ttc | aaa | gac | gct | gga | agc | acc | att | gat | gag | aat | 1080  |
| Tyr | Thr | Val | Ser | Ile | Phe | Lys | Asp | Ala | Gly | Ser | Thr | Ile | Asp | Glu | Asn |       |
| 305 |     |     |     |     | 310 |     |     |     |     | 315 |     |     |     |     | 320 |       |
| ctc | tgc | aca | att | att | gtt | ggt | gtt | gtt | aat | ttt | ggc | gca | aca | ttc | ttt | 1128  |
| Leu | Cys | Thr | Ile | Ile | Val | Gly | Val | Val | Asn | Phe | Gly | Ala | Thr | Phe | Phe |       |
|     |     |     |     | 325 |     |     |     |     | 330 |     |     |     |     | 335 |     |       |
| gct | acc | gtt | ctt | att | gat | cgt | ctt | gga | cgt | aaa | att | ctt | ttg | tac | atc | 1176  |
| Ala | Thr | Val | Leu | Ile | Asp | Arg | Leu | Gly | Arg | Lys | Ile | Leu | Leu | Tyr | Ile |       |
|     |     |     | 340 |     |     |     |     | 345 |     |     |     |     | 350 |     |     |       |
| tct | gaa | gta | gca | atg | gta | att | act | cta | ttg | aca | tta | gga | aca | ttc | ttt | 1224  |
| Ser | Glu | Val | Ala | Met | Val | Ile | Thr | Leu | Leu | Thr | Leu | Gly | Thr | Phe | Phe |       |
| 355 |     |     |     |     |     | 360 |     |     |     |     | 365 |     |     |     |     |       |
| tac | tat | aaa | aat | tct | gga | aat | gat | gtc | tca | aat | att | gga | tgg | cta | cca | 1272  |
| Tyr | Tyr | Lys | Asn | Ser | Gly | Asn | Asp | Val | Ser | Asn | Ile | Gly | Trp | Leu | Pro |       |
| 370 |     |     |     |     | 375 |     |     |     |     | 380 |     |     |     |     |     |       |
| ttg | gct | agc | ttt | gtt | att | tat | gtt | atc | gga | ttc | agt | tca | ggt | gtg | ggc | 1320  |
| Leu | Ala | Ser | Phe | Val | Ile | Tyr | Val | Ile | Gly | Phe | Ser | Ser | Gly | Val | Gly |       |
| 385 |     |     |     |     | 390 |     |     |     |     | 395 |     |     |     |     | 400 |       |
| cca | att | cca | tgg | ttg | atg | ttg | ggt | gaa | atc | tta | cca | gga | aaa | att | aga | 1368  |
| Pro | Ile | Pro | Trp | Leu | Met | Leu | Gly | Glu | Ile | Leu | Pro | Gly | Lys | Ile | Arg |       |
|     |     |     |     | 405 |     |     |     |     | 410 |     |     |     |     | 415 |     |       |
| gga | tca | gca | gct | tca | gtt | gca | act | gga | ttt | aac | tgg | aca | tgt | aca | ttc | 1416  |
| Gly | Ser | Ala | Ala | Ser | Val | Ala | Thr | Gly | Phe | Asn | Trp | Thr | Cys | Thr | Phe |       |
|     |     |     | 420 |     |     |     |     | 425 |     |     |     |     | 430 |     |     |       |
| att | gta | aca | aag | acg | ttt | gct | gat | ata | gtt | gct | gct | atc | ggt | aat | cat | 1464  |
| Ile | Val | Thr | Lys | Thr | Phe | Ala | Asp | Ile | Val | Ala | Ala | Ile | Gly | Asn | His |       |
|     |     | 435 |     |     |     |     | 440 |     |     |     |     | 445 |     |     |     |       |
| gga | gca | ttt | tgg | ttc | ttt | ggt | gtg | att | tgt | ctt | att | ggt | ctc | ttc | ttc | 1512  |
| Gly | Ala | Phe | Trp | Phe | Phe | Gly | Val | Ile | Cys | Leu | Ile | Gly | Leu | Phe | Phe |       |
|     | 450 |     |     |     |     | 455 |     |     |     |     | 460 |     |     |     |     |       |
| gtt | ata | ttc | ttt | gta | cca | gag | aca | cag | ggc | aaa | tca | tta | gaa | gag | att | 1560  |
| Val | Ile | Phe | Phe | Val | Pro | Glu | Thr | Gln | Gly | Lys | Ser | Leu | Glu | Glu | Ile |       |
| 465 |     |     |     |     | 470 |     |     |     |     | 475 |     |     |     |     | 480 |       |
| gag | aga | aaa | atg | atg | gga | cga | gta | aga | cgc | atg | tca | tca | gtc | gcg | aat | 1608  |
| Glu | Arg | Lys | Met | Met | Gly | Arg | Val | Arg | Arg | Met | Ser | Ser | Val | Ala | Asn |       |
|     |     |     |     | 485 |     |     |     |     | 490 |     |     |     |     | 495 |     |       |
| atg | aaa | cca | tta | agc | ttc | aat | atg | taa | ccataggaca | | | aagtatacat | | | | 1655 |
| Met | Lys | Pro | Leu | Ser | Phe | Asn | Met |     |     |     |     |     |     |     |     |       |
|     |     |     | 500 |     |     |     |     |     |     |     |     |     |     |     |     |       |

```
actatttac  gtgttttact  ttatttctc  acacctcctt  attttaact  gacatcaagc   1715 caaaaatta  tttttcaaat  gaccatgcat  aataatgatg  ataatagatt  tttaggtaga   1775
cgtagactgc  agtaaaagta  gaaatagaca  atgatttaa  aaaggaaat  tgttttagat   1835 gaatttatat  ttgtatctga  tttaatcagt  ttgattattg  tgataaagag  agaaaatttc   1895
aataatttgg  acatatgttt  ttcgaataag  ctggataata  ttgtgaaata  attgcaagat   1955
gcaagatgcg  aatggaaatt  tttttatcgt  taaatagata  tccacatata  aattgctgag   2015
ttcaaaattg  aatctcaata  attttgccat  aattttagtt  ttaaaccatg  ttatttgatt   2075
aatgcttatt  tgagtatagc  ctttataggc  ttttaaatta  gttgacattt  gcaatataaa   2135
caagttagtt  tatgaatgat  gatgtagata  gtaaggaac  acatacacta  atattttatta  2195 caacttcatt  tctggataaa  aattttcaa  gttcctttt  tcaataaaaa  ataatagtgt   2255
atcccatgac  acaacttatt  ttaatataac  aataaaattt  agaacataa  aacagtaaaa   2315
```

```
aaaaaaaaaa aaaaaaaaaa aa                                              2337
```

<210> SEQ ID NO 2
<211> LENGTH: 504
<212> TYPE: PRT
<213> ORGANISM: Polypedilum vanderplanki

<400> SEQUENCE: 2

```
Met Glu Leu Asn Asn Lys Glu Asp Ser Pro Arg His Thr Val Pro Phe
1               5                   10                  15

Val Arg Gln Ile Thr Glu Asp Gly Lys Ala Lys Leu Glu Ile Tyr Arg
            20                  25                  30

Pro Thr Thr Asn Pro Ile Tyr Ile Tyr Thr Gln Ile Leu Ala Ala Ile
        35                  40                  45

Ala Val Ser Met Gly Ser Met Val Val Gly Phe Ala Ser Ala Tyr Thr
    50                  55                  60

Ser Pro Ala Leu Val Ser Met Gln Asn Thr Thr Ile Thr Ser Phe Lys
65                  70                  75                  80

Val Thr Glu Gln Glu Ala Ser Trp Val Gly Gly Ile Met Pro Leu Ala
                85                  90                  95

Gly Leu Ala Gly Gly Ile Ala Gly Gly Pro Phe Ile Glu Tyr Leu Gly
            100                 105                 110

Arg Lys Asn Thr Ile Leu Ala Thr Ala Val Pro Phe Ile Val Ala Trp
        115                 120                 125

Leu Leu Ile Ala Phe Ala Asn Ser Ile Trp Met Val Leu Ala Gly Arg
    130                 135                 140

Ala Leu Ser Gly Phe Cys Val Gly Ile Ala Ser Leu Ser Leu Pro Val
145                 150                 155                 160

Tyr Leu Gly Glu Thr Val Gln Pro Glu Val Arg Gly Thr Leu Gly Leu
                165                 170                 175

Leu Pro Thr Ala Phe Gly Asn Ile Gly Ile Leu Ile Cys Phe Val Ala
            180                 185                 190

Gly Lys Tyr Val Asn Trp Ser Gly Leu Ala Phe Ile Gly Ser Ile Leu
        195                 200                 205

Pro Ile Pro Phe Met Val Leu Thr Leu Ile Pro Glu Thr Pro Arg
    210                 215                 220

Trp Phe Val Thr Arg Gly Arg Glu Glu Arg Ala Arg Lys Ala Leu Gln
225                 230                 235                 240

Trp Leu Arg Gly Lys Lys Ala Asp Val Glu Pro Glu Leu Lys Gly Ile
                245                 250                 255

Val Lys Ser His Cys Glu Ala Glu Arg His Ala Ser Gln Asn Ala Ile
            260                 265                 270

Phe Asp Leu Met Lys Arg Ser Asn Leu Lys Pro Leu Leu Ile Ala Leu
        275                 280                 285

Gly Leu Met Phe Phe Gln Gln Leu Ser Gly Ile Asn Ala Val Ile Phe
    290                 295                 300

Tyr Thr Val Ser Ile Phe Lys Asp Ala Gly Ser Thr Ile Asp Glu Asn
305                 310                 315                 320

Leu Cys Thr Ile Ile Val Gly Val Val Asn Phe Gly Ala Thr Phe Phe
                325                 330                 335

Ala Thr Val Leu Ile Asp Arg Leu Gly Arg Lys Ile Leu Leu Tyr Ile
            340                 345                 350

Ser Glu Val Ala Met Val Ile Thr Leu Leu Thr Leu Gly Thr Phe Phe
        355                 360                 365
```

```
Tyr Tyr Lys Asn Ser Gly Asn Asp Val Ser Asn Ile Gly Trp Leu Pro
        370                 375                 380

Leu Ala Ser Phe Val Ile Tyr Val Ile Gly Phe Ser Ser Gly Val Gly
385                 390                 395                 400

Pro Ile Pro Trp Leu Met Leu Gly Glu Ile Leu Pro Gly Lys Ile Arg
                405                 410                 415

Gly Ser Ala Ala Ser Val Ala Thr Gly Phe Asn Trp Thr Cys Thr Phe
            420                 425                 430

Ile Val Thr Lys Thr Phe Ala Asp Ile Val Ala Ala Ile Gly Asn His
        435                 440                 445

Gly Ala Phe Trp Phe Phe Gly Val Ile Cys Leu Ile Gly Leu Phe Phe
    450                 455                 460

Val Ile Phe Phe Val Pro Glu Thr Gln Gly Lys Ser Leu Glu Glu Ile
465                 470                 475                 480

Glu Arg Lys Met Met Gly Arg Val Arg Arg Met Ser Ser Val Ala Asn
                485                 490                 495

Met Lys Pro Leu Ser Phe Asn Met
            500

<210> SEQ ID NO 3
<211> LENGTH: 1521
<212> TYPE: DNA
<213> ORGANISM: Drosophila melanogaster
<220> FEATURE:
<221> NAME/KEY: CDS
<222> LOCATION: (1)..(1521)

<400> SEQUENCE: 3 atg gac gag atg gac aac aaa cgc ggc gag aac atc cgt cat gcg gtg    48
Met Asp Glu Met Asp Asn Lys Arg Gly Glu Asn Ile Arg His Ala Val
1               5                   10                  15 ccc ttc gtg cgc cag ata acc gag gat ggc aag ccc aag ctg gag gtc    96
Pro Phe Val Arg Gln Ile Thr Glu Asp Gly Lys Pro Lys Leu Glu Val
                20                  25                  30 tac cgt ccc aca acg aat ccc ata tac att tgg aca cag gtc ttg gct   144
Tyr Arg Pro Thr Thr Asn Pro Ile Tyr Ile Trp Thr Gln Val Leu Ala
            35                  40                  45 gct ctg agt gtc tcg ctg ggc tcc cta gtg gtc gga ttt gtc agc gct   192
Ala Leu Ser Val Ser Leu Gly Ser Leu Val Val Gly Phe Val Ser Ala
        50                  55                  60 tac acg tcg cct gca ctt gtg tcg atg acc gat cgg aat atc acc tcg   240
Tyr Thr Ser Pro Ala Leu Val Ser Met Thr Asp Arg Asn Ile Thr Ser
65                  70                  75                  80 ttt gag gtc acc caa gat gct ggt tct tgg gtt ggt ggc atc atg ccg   288
Phe Glu Val Thr Gln Asp Ala Gly Ser Trp Val Gly Gly Ile Met Pro
                85                  90                  95 ctg gct gga ttg gca ggt ggc ata gcc gga gga ccc ttg att gaa tat   336
Leu Ala Gly Leu Ala Gly Gly Ile Ala Gly Gly Pro Leu Ile Glu Tyr
                100                 105                 110 ctg ggc agg cgc aac acc atc ctg gcc acc gcg gtg ccc ttc att gtc   384
Leu Gly Arg Arg Asn Thr Ile Leu Ala Thr Ala Val Pro Phe Ile Val
            115                 120                 125 tca tca cta ctg att gcc tgt gct gtg aat gtg gct atg gtt ctg tgc   432
Ser Ser Leu Leu Ile Ala Cys Ala Val Asn Val Ala Met Val Leu Cys
        130                 135                 140 gga cga ttc ctg gct gga ttc tgc gtt ggc att gcc tct tta tcc ctg   480
Gly Arg Phe Leu Ala Gly Phe Cys Val Gly Ile Ala Ser Leu Ser Leu
145                 150                 155                 160 ccc gtc tac ctg ggt gaa act gtg cag cct gag gtg cga ggc act ttg   528
```

```
                Pro Val Tyr Leu Gly Glu Thr Val Gln Pro Glu Val Arg Gly Thr Leu
                                165                 170                 175 ggt ttg ctg ccc acg gcc ttt ggt aac ata ggc atc ctg ctc tgc ttc            576
Gly Leu Leu Pro Thr Ala Phe Gly Asn Ile Gly Ile Leu Leu Cys Phe
            180                 185                 190 gtg gcg gga tcc ttt atg aat tgg tcg atg ctg gcc ttc ttg gga gct            624
Val Ala Gly Ser Phe Met Asn Trp Ser Met Leu Ala Phe Leu Gly Ala
        195                 200                 205 gct ctg ccc gtt ccc ttc ctg att tta atg ttc ctt att ccg gaa act            672
Ala Leu Pro Val Pro Phe Leu Ile Leu Met Phe Leu Ile Pro Glu Thr
    210                 215                 220 ccg cgc tgg ttt gtt ggc cgt ggt ctg gag gag cgc gcc agg aag gct            720
Pro Arg Trp Phe Val Gly Arg Gly Leu Glu Glu Arg Ala Arg Lys Ala
225                 230                 235                 240 ttg aaa tgg ctg cgt ggc aag gag gct gat gtg gag ccc gaa ctg aag            768
Leu Lys Trp Leu Arg Gly Lys Glu Ala Asp Val Glu Pro Glu Leu Lys
                245                 250                 255 ggt ttg atg cga tcc cag gcc gat gcc gat cgt cag gca tcg cgg aac            816
Gly Leu Met Arg Ser Gln Ala Asp Ala Asp Arg Gln Ala Ser Arg Asn
            260                 265                 270 acc atg ctg gag ctg ctt aag ctc aac aat ctg aag cca cta tca att            864
Thr Met Leu Glu Leu Leu Lys Leu Asn Asn Leu Lys Pro Leu Ser Ile
        275                 280                 285 tcc ttg ggt ctg atg ttc ttc caa cag ttc agc ggt atc aac gcg gtt            912
Ser Leu Gly Leu Met Phe Phe Gln Gln Phe Ser Gly Ile Asn Ala Val
    290                 295                 300 atc ttc tac acg gtc cag atc ttc aag gat gcg gga tct acc att gat            960
Ile Phe Tyr Thr Val Gln Ile Phe Lys Asp Ala Gly Ser Thr Ile Asp
305                 310                 315                 320 ggc aat ctc tgc acg atc att gtg gga att gtt aac ttt ttg gct acg           1008
Gly Asn Leu Cys Thr Ile Ile Val Gly Ile Val Asn Phe Leu Ala Thr
                325                 330                 335 ttt ata ggc atc gtt ctg att gat cgg gcg ggc aga aag att ctt cta           1056
Phe Ile Gly Ile Val Leu Ile Asp Arg Ala Gly Arg Lys Ile Leu Leu
            340                 345                 350 tat gtc tcc gat atc gcc atg gtc ctg acc ctg ttc gtt ctg ggc ggc           1104
Tyr Val Ser Asp Ile Ala Met Val Leu Thr Leu Phe Val Leu Gly Gly
        355                 360                 365 ttc ttc tat tgc aag acg tat ggt ccg gat gtg tcc cat ttg ggt tgg           1152
Phe Phe Tyr Cys Lys Thr Tyr Gly Pro Asp Val Ser His Leu Gly Trp
    370                 375                 380 ttg cca ctc act tgc ttc gtc atc tac att ctg gga ttc tcc ctg ggc           1200
Leu Pro Leu Thr Cys Phe Val Ile Tyr Ile Leu Gly Phe Ser Leu Gly
385                 390                 395                 400 ttc gga ccc att ccc tgg ctg atg atg ggt gag att ctg ccg gcc aaa           1248
Phe Gly Pro Ile Pro Trp Leu Met Met Gly Glu Ile Leu Pro Ala Lys
                405                 410                 415 att cgc gga tcg gct gcc tcg gtg gcc acg gct ttc aac tgg ttc tgc           1296
Ile Arg Gly Ser Ala Ala Ser Val Ala Thr Ala Phe Asn Trp Phe Cys
            420                 425                 430 acg ttt gtg gtg acc aag acc ttc cag gac ctc acg gtt gct atg ggc           1344
Thr Phe Val Val Thr Lys Thr Phe Gln Asp Leu Thr Val Ala Met Gly
        435                 440                 445 gcg cat gga gcg ttc tgg cta ttc ggc gcc atc tgc ttc gtg ggt ctg           1392
Ala His Gly Ala Phe Trp Leu Phe Gly Ala Ile Cys Phe Val Gly Leu
    450                 455                 460 ttc ttt gtg ata atc tac gtg ccc gaa acg cag ggc aag acg ctg gag           1440
Phe Phe Val Ile Ile Tyr Val Pro Glu Thr Gln Gly Lys Thr Leu Glu
465                 470                 475                 480
```

```
gac atc gag cgg aag atg atg ggc cgt gtg cgc cgc atg tcc tcg gtg        1488
Asp Ile Glu Arg Lys Met Met Gly Arg Val Arg Arg Met Ser Ser Val
            485                 490                 495 gcc aat atc aag cca ttg tcc ttc aac atg taa                            1521
Ala Asn Ile Lys Pro Leu Ser Phe Asn Met
        500                 505
```

<210> SEQ ID NO 4
<211> LENGTH: 506
<212> TYPE: PRT
<213> ORGANISM: Drosophila melanogaster

<400> SEQUENCE: 4

```
Met Asp Glu Met Asp Asn Lys Arg Gly Glu Asn Ile Arg His Ala Val
1               5                   10                  15

Pro Phe Val Arg Gln Ile Thr Glu Asp Gly Lys Pro Lys Leu Glu Val
            20                  25                  30

Tyr Arg Pro Thr Thr Asn Pro Ile Tyr Ile Trp Thr Gln Val Leu Ala
        35                  40                  45

Ala Leu Ser Val Ser Leu Gly Ser Leu Val Val Gly Phe Val Ser Ala
    50                  55                  60

Tyr Thr Ser Pro Ala Leu Val Ser Met Thr Asp Arg Asn Ile Thr Ser
65                  70                  75                  80

Phe Glu Val Thr Gln Asp Ala Gly Ser Trp Val Gly Gly Ile Met Pro
                85                  90                  95

Leu Ala Gly Leu Ala Gly Gly Ile Ala Gly Gly Pro Leu Ile Glu Tyr
            100                 105                 110

Leu Gly Arg Arg Asn Thr Ile Leu Ala Thr Ala Val Pro Phe Ile Val
        115                 120                 125

Ser Ser Leu Leu Ile Ala Cys Ala Val Asn Val Ala Met Val Leu Cys
    130                 135                 140

Gly Arg Phe Leu Ala Gly Phe Cys Val Gly Ile Ala Ser Leu Ser Leu
145                 150                 155                 160

Pro Val Tyr Leu Gly Glu Thr Val Gln Pro Glu Val Arg Gly Thr Leu
                165                 170                 175

Gly Leu Leu Pro Thr Ala Phe Gly Asn Ile Gly Ile Leu Leu Cys Phe
            180                 185                 190

Val Ala Gly Ser Phe Met Asn Trp Ser Met Leu Ala Phe Leu Gly Ala
        195                 200                 205

Ala Leu Pro Val Pro Phe Leu Ile Leu Met Phe Leu Ile Pro Glu Thr
    210                 215                 220

Pro Arg Trp Phe Val Gly Arg Gly Leu Glu Glu Arg Ala Arg Lys Ala
225                 230                 235                 240

Leu Lys Trp Leu Arg Gly Lys Glu Ala Asp Val Glu Pro Glu Leu Lys
                245                 250                 255

Gly Leu Met Arg Ser Gln Ala Asp Ala Asp Arg Gln Ala Ser Arg Asn
            260                 265                 270

Thr Met Leu Glu Leu Leu Lys Leu Asn Asn Leu Lys Pro Leu Ser Ile
        275                 280                 285

Ser Leu Gly Leu Met Phe Phe Gln Gln Phe Ser Gly Ile Asn Ala Val
    290                 295                 300

Ile Phe Tyr Thr Val Gln Ile Phe Lys Asp Ala Gly Ser Thr Ile Asp
305                 310                 315                 320

Gly Asn Leu Cys Thr Ile Ile Val Gly Ile Val Asn Phe Leu Ala Thr
                325                 330                 335
```

```
Phe Ile Gly Ile Val Leu Ile Asp Arg Ala Gly Arg Lys Ile Leu Leu
                    340                 345                 350

Tyr Val Ser Asp Ile Ala Met Val Leu Thr Leu Phe Val Leu Gly Gly
                355                 360                 365

Phe Phe Tyr Cys Lys Thr Tyr Gly Pro Asp Val Ser His Leu Gly Trp
            370                 375                 380

Leu Pro Leu Thr Cys Phe Val Ile Tyr Ile Leu Gly Phe Ser Leu Gly
385                 390                 395                 400

Phe Gly Pro Ile Pro Trp Leu Met Met Gly Glu Ile Leu Pro Ala Lys
                405                 410                 415

Ile Arg Gly Ser Ala Ala Ser Val Ala Thr Ala Phe Asn Trp Phe Cys
                420                 425                 430

Thr Phe Val Val Thr Lys Thr Phe Gln Asp Leu Thr Val Ala Met Gly
            435                 440                 445

Ala His Gly Ala Phe Trp Leu Phe Gly Ala Ile Cys Phe Val Gly Leu
        450                 455                 460

Phe Phe Val Ile Ile Tyr Val Pro Glu Thr Gln Gly Lys Thr Leu Glu
465                 470                 475                 480

Asp Ile Glu Arg Lys Met Met Gly Arg Val Arg Arg Met Ser Ser Val
                485                 490                 495

Ala Asn Ile Lys Pro Leu Ser Phe Asn Met
            500                 505

<210> SEQ ID NO 5
<211> LENGTH: 1515
<212> TYPE: DNA
<213> ORGANISM: Anopheles gambiae
<220> FEATURE:
<221> NAME/KEY: CDS
<222> LOCATION: (1)..(1515)

<400> SEQUENCE: 5 atg gaa atg ggc acg aaa gag gag aat atg cgc acc gcc gtc ccg ttc     48
Met Glu Met Gly Thr Lys Glu Glu Asn Met Arg Thr Ala Val Pro Phe
1               5                   10                  15 gtg cga cag atc acc gag gaa ggc aaa ccg aag ctg gag gtg tac cgg     96
Val Arg Gln Ile Thr Glu Glu Gly Lys Pro Lys Leu Glu Val Tyr Arg
            20                  25                  30 cca acc aca aat ccg atc tac atc tgg aca cag gta ctg gcc gcc ctg    144
Pro Thr Thr Asn Pro Ile Tyr Ile Trp Thr Gln Val Leu Ala Ala Leu
        35                  40                  45 tcg gtg tcg ctc ggc tcc atg gtc gtg gga ttt tcg tcc gcc tac acc    192
Ser Val Ser Leu Gly Ser Met Val Val Gly Phe Ser Ser Ala Tyr Thr
    50                  55                  60 tca ccc gcc ctg gta tcg atg aag gat cgc aac att aca tcg ttc gag    240
Ser Pro Ala Leu Val Ser Met Lys Asp Arg Asn Ile Thr Ser Phe Glu
65                  70                  75                  80 gtt acg gac caa tcg ggc tcg tgg gtc ggt ggt att atg ccg ctc gcc    288
Val Thr Asp Gln Ser Gly Ser Trp Val Gly Gly Ile Met Pro Leu Ala
                85                  90                  95 ggt ttg gcc ggt ggt att ctc ggc ggg cca atg att gag tat ctc ggg    336
Gly Leu Ala Gly Gly Ile Leu Gly Gly Pro Met Ile Glu Tyr Leu Gly
            100                 105                 110 cgc aag aac acc atc ctg gca acg gca aca ccg ttc atc att tcc tgg    384
Arg Lys Asn Thr Ile Leu Ala Thr Ala Thr Pro Phe Ile Ile Ser Trp
        115                 120                 125 ctg ctg atc ggt tgc gcc acg cat gtc gca atg gtt ttg gtt ggt cgt    432
Leu Leu Ile Gly Cys Ala Thr His Val Ala Met Val Leu Val Gly Arg
    130                 135                 140
```

| | | |
|---|---|---|
| gca ctg tcc ggt ttg tgt gtc ggt atc gct tcc ctc tcg ctt ccg gtc<br>Ala Leu Ser Gly Leu Cys Val Gly Ile Ala Ser Leu Ser Leu Pro Val<br>145                          150                     155                    160 | | 480 |
| tat ctc ggc gaa acg gta cag ccg gag gtg cgc ggt acg ctc ggc ctg<br>Tyr Leu Gly Glu Thr Val Gln Pro Glu Val Arg Gly Thr Leu Gly Leu<br>                  165                     170                     175 | | 528 |
| ctt ccg acc gcc ttc ggt aac atc ggc atc ctg ctg tgc ttc gtc gcg<br>Leu Pro Thr Ala Phe Gly Asn Ile Gly Ile Leu Leu Cys Phe Val Ala<br>                  180                     185                     190 | | 576 |
| ggc aaa tat ctg gac tgg tcg ggg ctg gca ttc ctc ggt gca gcg ctc<br>Gly Lys Tyr Leu Asp Trp Ser Gly Leu Ala Phe Leu Gly Ala Ala Leu<br>               195                     200                     205 | | 624 |
| ccg ata ccg ttc ctg ttg ctg atg ttc ctc att ccc gag acg ccc cgc<br>Pro Ile Pro Phe Leu Leu Leu Met Phe Leu Ile Pro Glu Thr Pro Arg<br>210                          215                     220 | | 672 |
| tgg tac gtg tcg cgc aac cgg gag gat cgt gca cgc aaa gcg ctc cag<br>Trp Tyr Val Ser Arg Asn Arg Glu Asp Arg Ala Arg Lys Ala Leu Gln<br>225                          230                     235                     240 | | 720 |
| tgg ctg cgc ggt cgc aag gcg gat gtg gag ccg gag ctg aag ggc atc<br>Trp Leu Arg Gly Arg Lys Ala Asp Val Glu Pro Glu Leu Lys Gly Ile<br>                  245                     250                     255 | | 768 |
| tcg aaa tcg cac cag gac gcg gaa cgg cac gcc tct agc agc gcc atg<br>Ser Lys Ser His Gln Asp Ala Glu Arg His Ala Ser Ser Ser Ala Met<br>               260                     265                     270 | | 816 |
| ctg gat ctg ctc aac aag gcc aac ctg aag ccg ctg ctc att tcg ctc<br>Leu Asp Leu Leu Asn Lys Ala Asn Leu Lys Pro Leu Leu Ile Ser Leu<br>                  275                     280                     285 | | 864 |
| gga ctg atg ttc ttc cag cag ctg tcc ggt atc aat gcg gtc atc ttc<br>Gly Leu Met Phe Phe Gln Gln Leu Ser Gly Ile Asn Ala Val Ile Phe<br>290                          295                     300 | | 912 |
| tac acg gtg cag atc ttc cag agc gcc ggc tcg acg atc gac gag aag<br>Tyr Thr Val Gln Ile Phe Gln Ser Ala Gly Ser Thr Ile Asp Glu Lys<br>305                          310                     315                     320 | | 960 |
| ctg tgc acg atc atc gtc ggt gtg gtg aac ttt atc gcc acc ttc atc<br>Leu Cys Thr Ile Ile Val Gly Val Val Asn Phe Ile Ala Thr Phe Ile<br>                  325                     330                     335 | | 1008 |
| gcg acc gtg ctg atc gat cgg ctc ggc cgc aag ata ctg ctg tac atc<br>Ala Thr Val Leu Ile Asp Arg Leu Gly Arg Lys Ile Leu Leu Tyr Ile<br>                  340                     345                     350 | | 1056 |
| tcg gac gtg gcc atg atc att acg ctc atg acg ctc ggc acg ttc ttc<br>Ser Asp Val Ala Met Ile Ile Thr Leu Met Thr Leu Gly Thr Phe Phe<br>               355                     360                     365 | | 1104 |
| tac atg aag aac aac ggt gac gat gtg tcc gag atc ggt tgg ttg ccg<br>Tyr Met Lys Asn Asn Gly Asp Asp Val Ser Glu Ile Gly Trp Leu Pro<br>370                          375                     380 | | 1152 |
| ctg gcc gcg ttc gtt gtg ttc gtc gta ggc ttc tcg ctc ggg ttc ggc<br>Leu Ala Ala Phe Val Val Phe Val Val Gly Phe Ser Leu Gly Phe Gly<br>385                          390                     395                     400 | | 1200 |
| ccc att ccg tgg ctg atg atg ggt gag att ctg ccg ggc aag att cgc<br>Pro Ile Pro Trp Leu Met Met Gly Glu Ile Leu Pro Gly Lys Ile Arg<br>                  405                     410                     415 | | 1248 |
| ggt tcg gcc gcg tcc gtt gcg acg gca ttc aac tgg agc tgc acg ttc<br>Gly Ser Ala Ala Ser Val Ala Thr Ala Phe Asn Trp Ser Cys Thr Phe<br>                  420                     425                     430 | | 1296 |
| gtg gtg acg aag acg ttc gct gac att acc gcc tcc atc ggt aat cac<br>Val Val Thr Lys Thr Phe Ala Asp Ile Thr Ala Ser Ile Gly Asn His<br>435                          440                     445 | | 1344 |
| ggt gca ttc tgg atg ttc ggt tcg atc tgt atc gtc ggt ctg ctg ttt<br>Gly Ala Phe Trp Met Phe Gly Ser Ile Cys Ile Val Gly Leu Leu Phe | | 1392 |

```
                450                 455                 460
gtg atc gtg tac gtg ccg gag acg cag ggc aaa tcg ctc gag gac att    1440
Val Ile Val Tyr Val Pro Glu Thr Gln Gly Lys Ser Leu Glu Asp Ile
465                 470                 475                 480 gag cgc aag atg atg ggt cgc gtg cgg cgc atg agc tcg gtg gcc aac    1488
Glu Arg Lys Met Met Gly Arg Val Arg Arg Met Ser Ser Val Ala Asn
                485                 490                 495 atc aag ccg ctg tcg ttc aac atg taa                                1515
Ile Lys Pro Leu Ser Phe Asn Met
                500

<210> SEQ ID NO 6
<211> LENGTH: 504
<212> TYPE: PRT
<213> ORGANISM: Anopheles gambiae

<400> SEQUENCE: 6

Met Glu Met Gly Thr Lys Glu Glu Asn Met Arg Thr Ala Val Pro Phe
1               5                   10                  15

Val Arg Gln Ile Thr Glu Glu Gly Lys Pro Lys Leu Glu Val Tyr Arg
                20                  25                  30

Pro Thr Thr Asn Pro Ile Tyr Ile Trp Thr Gln Val Leu Ala Ala Leu
            35                  40                  45

Ser Val Ser Leu Gly Ser Met Val Val Gly Phe Ser Ser Ala Tyr Thr
        50                  55                  60

Ser Pro Ala Leu Val Ser Met Lys Asp Arg Asn Ile Thr Ser Phe Glu
65                  70                  75                  80

Val Thr Asp Gln Ser Gly Ser Trp Val Gly Gly Ile Met Pro Leu Ala
                85                  90                  95

Gly Leu Ala Gly Gly Ile Leu Gly Gly Pro Met Ile Glu Tyr Leu Gly
            100                 105                 110

Arg Lys Asn Thr Ile Leu Ala Thr Ala Thr Pro Phe Ile Ile Ser Trp
        115                 120                 125

Leu Leu Ile Gly Cys Ala Thr His Val Ala Met Val Leu Val Gly Arg
130                 135                 140

Ala Leu Ser Gly Leu Cys Val Gly Ile Ala Ser Leu Ser Leu Pro Val
145                 150                 155                 160

Tyr Leu Gly Glu Thr Val Gln Pro Glu Val Arg Gly Thr Leu Gly Leu
                165                 170                 175

Leu Pro Thr Ala Phe Gly Asn Ile Gly Ile Leu Leu Cys Phe Val Ala
            180                 185                 190

Gly Lys Tyr Leu Asp Trp Ser Gly Leu Ala Phe Leu Gly Ala Ala Leu
        195                 200                 205

Pro Ile Pro Phe Leu Leu Leu Met Phe Leu Ile Pro Glu Thr Pro Arg
210                 215                 220

Trp Tyr Val Ser Arg Asn Arg Glu Asp Arg Ala Arg Lys Ala Leu Gln
225                 230                 235                 240

Trp Leu Arg Gly Arg Lys Ala Asp Val Glu Pro Glu Leu Lys Gly Ile
                245                 250                 255

Ser Lys Ser His Gln Asp Ala Glu Arg His Ala Ser Ser Ser Ala Met
            260                 265                 270

Leu Asp Leu Leu Asn Lys Ala Asn Leu Lys Pro Leu Leu Ile Ser Leu
        275                 280                 285

Gly Leu Met Phe Phe Gln Gln Leu Ser Gly Ile Asn Ala Val Ile Phe
290                 295                 300
```

-continued

```
Tyr Thr Val Gln Ile Phe Gln Ser Ala Gly Ser Thr Ile Asp Glu Lys
305                 310                 315                 320

Leu Cys Thr Ile Ile Val Gly Val Val Asn Phe Ile Ala Thr Phe Ile
            325                 330                 335

Ala Thr Val Leu Ile Asp Arg Leu Gly Arg Lys Ile Leu Leu Tyr Ile
        340                 345                 350

Ser Asp Val Ala Met Ile Ile Thr Leu Met Thr Leu Gly Thr Phe Phe
    355                 360                 365

Tyr Met Lys Asn Asn Gly Asp Asp Val Ser Glu Ile Gly Trp Leu Pro
370                 375                 380

Leu Ala Ala Phe Val Val Phe Val Val Gly Phe Ser Leu Gly Phe Gly
385                 390                 395                 400

Pro Ile Pro Trp Leu Met Met Gly Glu Ile Leu Pro Gly Lys Ile Arg
            405                 410                 415

Gly Ser Ala Ala Ser Val Ala Thr Ala Phe Asn Trp Ser Cys Thr Phe
        420                 425                 430

Val Val Thr Lys Thr Phe Ala Asp Ile Thr Ala Ser Ile Gly Asn His
    435                 440                 445

Gly Ala Phe Trp Met Phe Gly Ser Ile Cys Ile Val Gly Leu Leu Phe
450                 455                 460

Val Ile Val Tyr Val Pro Glu Thr Gln Gly Lys Ser Leu Glu Asp Ile
465                 470                 475                 480

Glu Arg Lys Met Met Gly Arg Val Arg Arg Met Ser Ser Val Ala Asn
            485                 490                 495

Ile Lys Pro Leu Ser Phe Asn Met
            500

<210> SEQ ID NO 7
<211> LENGTH: 1512
<212> TYPE: DNA
<213> ORGANISM: Apis mellifera
<220> FEATURE:
<221> NAME/KEY: CDS
<222> LOCATION: (1)..(1509)

<400> SEQUENCE: 7 atg ggg gtc gaa aac acc aag caa acc atg agc tcg caa aat ata aaa      48
Met Gly Val Glu Asn Thr Lys Gln Thr Met Ser Ser Gln Asn Ile Lys
1               5                   10                  15 ccg gcc aag gat tcg gac gat gtt ttg cat aca cag ttc aaa gaa gtg      96
Pro Ala Lys Asp Ser Asp Asp Val Leu His Thr Gln Phe Lys Glu Val
            20                  25                  30 aaa cga tca cct atg cgc tat act atg cag ctg tta gct gct cta gcg     144
Lys Arg Ser Pro Met Arg Tyr Thr Met Gln Leu Leu Ala Ala Leu Ala
        35                  40                  45 gtg tca atg gcc tct ttg atg atc ggt tac tcc tct tcc tac acg tcc     192
Val Ser Met Ala Ser Leu Met Ile Gly Tyr Ser Ser Ser Tyr Thr Ser
    50                  55                  60 cct gct tta gtt tcg atg cga gat aac acg acg gcc acg ttc gaa gta     240
Pro Ala Leu Val Ser Met Arg Asp Asn Thr Thr Ala Thr Phe Glu Val
65                  70                  75                  80 act atg gat atg gct atg tgg ata gga tcg atc atg cca ctg agc gca     288
Thr Met Asp Met Ala Met Trp Ile Gly Ser Ile Met Pro Leu Ser Ala
            85                  90                  95 ctt att gga ggc ata atc ggt ggt cca tgt att gaa tac att ggt aga     336
Leu Ile Gly Gly Ile Ile Gly Gly Pro Cys Ile Glu Tyr Ile Gly Arg
            100                 105                 110 agg aac act att ctg agc act gcc tta ccg ttt ctt gca ggc tgg tta     384
```

```
                Arg Asn Thr Ile Leu Ser Thr Ala Leu Pro Phe Leu Ala Gly Trp Leu
                                115                 120                 125 ttt atc gca ttg gca aca aat gtt gcg atg ata ttg gtt gga cgc agt           432
Phe Ile Ala Leu Ala Thr Asn Val Ala Met Ile Leu Val Gly Arg Ser
130                 135                 140 ata tgc ggt ttc tgc gtc ggt gtc gct tct ctt tcc ttg cca gtt tat           480
Ile Cys Gly Phe Cys Val Gly Val Ala Ser Leu Ser Leu Pro Val Tyr
145                 150                 155                 160 ctt gga gaa tct ata caa cca gaa gta cgt ggt tca ctc ggt ctc tta           528
Leu Gly Glu Ser Ile Gln Pro Glu Val Arg Gly Ser Leu Gly Leu Leu
                165                 170                 175 cca acc gtc ttt ggt aat tca ggg atc tta atg tgc ttc aca gct gga           576
Pro Thr Val Phe Gly Asn Ser Gly Ile Leu Met Cys Phe Thr Ala Gly
            180                 185                 190 atg tat cta gct tgg cga aat ctt gca tta cta ggt gcc tgt ata ccg           624
Met Tyr Leu Ala Trp Arg Asn Leu Ala Leu Leu Gly Ala Cys Ile Pro
        195                 200                 205 ata ata ttt ttg att ctg atg ttc cta att cct gaa acg cca aga tgg           672
Ile Ile Phe Leu Ile Leu Met Phe Leu Ile Pro Glu Thr Pro Arg Trp
210                 215                 220 tac att tcg aaa ggg aaa ata aaa gag gca cga aaa tcg ttg caa tgg           720
Tyr Ile Ser Lys Gly Lys Ile Lys Glu Ala Arg Lys Ser Leu Gln Trp
225                 230                 235                 240 ttg cgg ggc aag act gcc gat att agc gag gaa tta gat tcc att caa           768
Leu Arg Gly Lys Thr Ala Asp Ile Ser Glu Glu Leu Asp Ser Ile Gln
                245                 250                 255 aaa atg cat atc gaa agt gaa cgt atc gct aca gag ggt gct ttg ata           816
Lys Met His Ile Glu Ser Glu Arg Ile Ala Thr Glu Gly Ala Leu Ile
            260                 265                 270 gaa ctt ttc agg aaa aat cat ata aaa ccg gtt ttt att tcc ctt ggc           864
Glu Leu Phe Arg Lys Asn His Ile Lys Pro Val Phe Ile Ser Leu Gly
        275                 280                 285 cta atg ttc ttt caa cag ttt tca gga atc aat gcg gtc ata ttt tac           912
Leu Met Phe Phe Gln Gln Phe Ser Gly Ile Asn Ala Val Ile Phe Tyr
290                 295                 300 aca gtt caa att ttc aag gac tct gga agc act gta gac gaa aat ctt           960
Thr Val Gln Ile Phe Lys Asp Ser Gly Ser Thr Val Asp Glu Asn Leu
305                 310                 315                 320 tcc acc atc atc gta ggt ctc gta aat ttc att tca acg ttc gtt gca          1008
Ser Thr Ile Ile Val Gly Leu Val Asn Phe Ile Ser Thr Phe Val Ala
                325                 330                 335 gca atg att ata gat aga ctg ggt cga aaa atg tta ctc tac ata agt          1056
Ala Met Ile Ile Asp Arg Leu Gly Arg Lys Met Leu Leu Tyr Ile Ser
            340                 345                 350 agt ata ctg atg tgt ata act cta ttc aca ttc ggt aca ttt ttc tat          1104
Ser Ile Leu Met Cys Ile Thr Leu Phe Thr Phe Gly Thr Phe Phe Tyr
        355                 360                 365 gtg aaa gaa tta atg gat gtt act gca ttt ggt tgg att cca ttg atg          1152
Val Lys Glu Leu Met Asp Val Thr Ala Phe Gly Trp Ile Pro Leu Met
370                 375                 380 agt ctg atc gtt tac gtg atc ggg ttc tca ttt ggt ttt ggt ccg atc          1200
Ser Leu Ile Val Tyr Val Ile Gly Phe Ser Phe Gly Phe Gly Pro Ile
385                 390                 395                 400 cca tgg tta atg atg ggc gaa att tta cca gtt aag ata cgt ggt acg          1248
Pro Trp Leu Met Met Gly Glu Ile Leu Pro Val Lys Ile Arg Gly Thr
                405                 410                 415 gct gcc agt gtt gca acg gct ttc aat tgg tcc tgt aca ttc gtc gtt          1296
Ala Ala Ser Val Ala Thr Ala Phe Asn Trp Ser Cys Thr Phe Val Val
            420                 425                 430
```

```
acg aaa act tac gaa gat ttg gtt tta cat atc ggc cca tat gga acc          1344
Thr Lys Thr Tyr Glu Asp Leu Val Leu His Ile Gly Pro Tyr Gly Thr
        435                 440                 445 ttt tgg ttg ttc ggt acg ctc gta gca gta gca ttc att ttt gta att          1392
Phe Trp Leu Phe Gly Thr Leu Val Ala Val Ala Phe Ile Phe Val Ile
450                 455                 460 att tgt gta cca gaa aca cga gga cga tct ctc gaa gaa atc gaa aga          1440
Ile Cys Val Pro Glu Thr Arg Gly Arg Ser Leu Glu Glu Ile Glu Arg
465                 470                 475                 480 aga ttc gct gga ccg gtg aga aga acg agc gcg atc gcc aat tta aaa          1488
Arg Phe Ala Gly Pro Val Arg Arg Thr Ser Ala Ile Ala Asn Leu Lys
                485                 490                 495 ccg atg cca ata acc att taa tga                                          1512
Pro Met Pro Ile Thr Ile
            500

<210> SEQ ID NO 8
<211> LENGTH: 502
<212> TYPE: PRT
<213> ORGANISM: Apis mellifera

<400> SEQUENCE: 8

Met Gly Val Glu Asn Thr Lys Gln Thr Met Ser Ser Gln Asn Ile Lys
1               5                   10                  15

Pro Ala Lys Asp Ser Asp Val Leu His Thr Gln Phe Lys Glu Val
            20                  25                  30

Lys Arg Ser Pro Met Arg Tyr Thr Met Gln Leu Leu Ala Ala Leu Ala
        35                  40                  45

Val Ser Met Ala Ser Leu Met Ile Gly Tyr Ser Ser Ser Tyr Thr Ser
    50                  55                  60

Pro Ala Leu Val Ser Met Arg Asp Asn Thr Thr Ala Thr Phe Glu Val
65                  70                  75                  80

Thr Met Asp Met Ala Met Trp Ile Gly Ser Ile Met Pro Leu Ser Ala
                85                  90                  95

Leu Ile Gly Gly Ile Ile Gly Gly Pro Cys Ile Glu Tyr Ile Gly Arg
            100                 105                 110

Arg Asn Thr Ile Leu Ser Thr Ala Leu Pro Phe Leu Ala Gly Trp Leu
        115                 120                 125

Phe Ile Ala Leu Ala Thr Asn Val Ala Met Ile Leu Val Gly Arg Ser
    130                 135                 140

Ile Cys Gly Phe Cys Val Gly Val Ala Ser Leu Ser Leu Pro Val Tyr
145                 150                 155                 160

Leu Gly Glu Ser Ile Gln Pro Glu Val Arg Gly Ser Leu Gly Leu Leu
                165                 170                 175

Pro Thr Val Phe Gly Asn Ser Gly Ile Leu Met Cys Phe Thr Ala Gly
            180                 185                 190

Met Tyr Leu Ala Trp Arg Asn Leu Ala Leu Leu Gly Ala Cys Ile Pro
        195                 200                 205

Ile Ile Phe Leu Ile Leu Met Phe Leu Ile Pro Glu Thr Pro Arg Trp
    210                 215                 220

Tyr Ile Ser Lys Gly Lys Ile Lys Glu Ala Arg Lys Ser Leu Gln Trp
225                 230                 235                 240

Leu Arg Gly Lys Thr Ala Asp Ile Ser Glu Glu Leu Asp Ser Ile Gln
                245                 250                 255

Lys Met His Ile Glu Ser Glu Arg Ile Ala Thr Glu Gly Ala Leu Ile
            260                 265                 270
```

```
Glu Leu Phe Arg Lys Asn His Ile Lys Pro Val Phe Ile Ser Leu Gly
            275                 280                 285

Leu Met Phe Gln Gln Phe Ser Gly Ile Asn Ala Val Ile Phe Tyr
        290                 295                 300

Thr Val Gln Ile Phe Lys Asp Ser Gly Ser Thr Val Asp Glu Asn Leu
305                 310                 315                 320

Ser Thr Ile Ile Val Gly Leu Val Asn Phe Ile Ser Thr Phe Val Ala
                325                 330                 335

Ala Met Ile Ile Asp Arg Leu Gly Arg Lys Met Leu Leu Tyr Ile Ser
                340                 345                 350

Ser Ile Leu Met Cys Ile Thr Leu Phe Thr Phe Gly Thr Phe Phe Tyr
            355                 360                 365

Val Lys Glu Leu Met Asp Val Thr Ala Phe Gly Trp Ile Pro Leu Met
        370                 375                 380

Ser Leu Ile Val Tyr Val Ile Gly Phe Ser Phe Gly Phe Gly Pro Ile
385                 390                 395                 400

Pro Trp Leu Met Met Gly Glu Ile Leu Pro Val Lys Ile Arg Gly Thr
                405                 410                 415

Ala Ala Ser Val Ala Thr Ala Phe Asn Trp Ser Cys Thr Phe Val Val
                420                 425                 430

Thr Lys Thr Tyr Glu Asp Leu Val Leu His Ile Gly Pro Tyr Gly Thr
            435                 440                 445

Phe Trp Leu Phe Gly Thr Leu Val Ala Val Ala Phe Ile Phe Val Ile
        450                 455                 460

Ile Cys Val Pro Glu Thr Arg Gly Arg Ser Leu Glu Glu Ile Glu Arg
465                 470                 475                 480

Arg Phe Ala Gly Pro Val Arg Arg Thr Ser Ala Ile Ala Asn Leu Lys
                485                 490                 495

Pro Met Pro Ile Thr Ile
            500

<210> SEQ ID NO 9
<211> LENGTH: 1521
<212> TYPE: DNA
<213> ORGANISM: Bombyx mori
<220> FEATURE:
<221> NAME/KEY: CDS
<222> LOCATION: (1)..(1518)

<400> SEQUENCE: 9 atg gaa atg gaa atc aag gac gag aac ttg cgg aat tct gtt cca ttc      48
Met Glu Met Glu Ile Lys Asp Glu Asn Leu Arg Asn Ser Val Pro Phe
1               5                   10                  15 gtt agg caa tta agc aca gac agc gtt aaa act aag acg gaa tac gat      96
Val Arg Gln Leu Ser Thr Asp Ser Val Lys Thr Lys Thr Glu Tyr Asp
            20                  25                  30 aac gag gat gga aca ccg tac aaa tct aca act cag aaa ctg ttt cta     144
Asn Glu Asp Gly Thr Pro Tyr Lys Ser Thr Thr Gln Lys Leu Phe Leu
        35                  40                  45 tgg acg cag ctt ctt gca gcg ttt gca gtt tct gtc ggt tca atg aat     192
Trp Thr Gln Leu Leu Ala Ala Phe Ala Val Ser Val Gly Ser Met Asn
    50                  55                  60 gtc gga ttt tca tct ggg tac aca tca cct gct gtg cta aca atg aat     240
Val Gly Phe Ser Ser Gly Tyr Thr Ser Pro Ala Val Leu Thr Met Asn
65                  70                  75                  80 ata act ttg gac ata aca aag gaa gaa ata aca tgg gtt ggg ggt ctt     288
Ile Thr Leu Asp Ile Thr Lys Glu Glu Ile Thr Trp Val Gly Gly Leu
                85                  90                  95
```

```
                                                        -continued atg ccg tta gca gct ttg gtc gga ggc att gtt ggc gga cct ttg atc      336
Met Pro Leu Ala Ala Leu Val Gly Gly Ile Val Gly Gly Pro Leu Ile
        100                 105                 110 gaa tac cta gga aga aaa aag aca att atg ggt aca gca gtg cca ttc      384
Glu Tyr Leu Gly Arg Lys Lys Thr Ile Met Gly Thr Ala Val Pro Phe
            115                 120                 125 acc atc gga tgg atg ttg atc gct aac gca att aac gtt gtg atg gta      432
Thr Ile Gly Trp Met Leu Ile Ala Asn Ala Ile Asn Val Val Met Val
130                 135                 140 ttt gct ggc cgg gtc ata tgc ggg gtg tgt gtg gga atc gta tct ctt      480
Phe Ala Gly Arg Val Ile Cys Gly Val Cys Val Gly Ile Val Ser Leu
145                 150                 155                 160 gca ttt ccg gtc tac att gga gaa act att caa ccg gag gtg aga gga      528
Ala Phe Pro Val Tyr Ile Gly Glu Thr Ile Gln Pro Glu Val Arg Gly
                165                 170                 175 gcc ttg ggt ctt ctg cca acc gcg ttt ggt aat aca gga ata ctt ttg      576
Ala Leu Gly Leu Leu Pro Thr Ala Phe Gly Asn Thr Gly Ile Leu Leu
            180                 185                 190 gcc ttc ttg gta gga tca tat ctg gat tgg tca aat tta gcg ttc ttt      624
Ala Phe Leu Val Gly Ser Tyr Leu Asp Trp Ser Asn Leu Ala Phe Phe
        195                 200                 205 ggg gca gca ata ccg gtg cca ttc ttc cta ctt atg att cta acc cca      672
Gly Ala Ala Ile Pro Val Pro Phe Phe Leu Leu Met Ile Leu Thr Pro
    210                 215                 220 gaa aca cct cgt tgg tat gtc tct aaa gca cgc gtc caa gaa gca cgc      720
Glu Thr Pro Arg Trp Tyr Val Ser Lys Ala Arg Val Gln Glu Ala Arg
225                 230                 235                 240 aaa tct ctg cgc tgg tta aga gga aag aat gta aat att gag aag gaa      768
Lys Ser Leu Arg Trp Leu Arg Gly Lys Asn Val Asn Ile Glu Lys Glu
                245                 250                 255 atg cgc gat tta aca ata tct caa acc gaa tcg gac aga act ggc gga      816
Met Arg Asp Leu Thr Ile Ser Gln Thr Glu Ser Asp Arg Thr Gly Gly
            260                 265                 270 aat gca ttc aaa cag tta ttc agt aaa aga tat ttg cca gct gtt atg      864
Asn Ala Phe Lys Gln Leu Phe Ser Lys Arg Tyr Leu Pro Ala Val Met
        275                 280                 285 att tct ttg gga ttg atg ctt ttc caa caa ctg act gga atc aac gct      912
Ile Ser Leu Gly Leu Met Leu Phe Gln Gln Leu Thr Gly Ile Asn Ala
    290                 295                 300 gtt ata ttc tac gca gca agt att ttc caa atg tct ggc agc agc gtc      960
Val Ile Phe Tyr Ala Ala Ser Ile Phe Gln Met Ser Gly Ser Ser Val
305                 310                 315                 320 gac gaa aac ttg gcc agt ata atc att gga gta gtg aat ttt att tca     1008
Asp Glu Asn Leu Ala Ser Ile Ile Ile Gly Val Val Asn Phe Ile Ser
                325                 330                 335 aca ttc ata gcg acc atg ctc atc gac cgc ctg gga aga aag gtg ttg     1056
Thr Phe Ile Ala Thr Met Leu Ile Asp Arg Leu Gly Arg Lys Val Leu
            340                 345                 350 ctg tac att tca tcg gta gcg atg atc acg aca ctc tta gca cta ggt     1104
Leu Tyr Ile Ser Ser Val Ala Met Ile Thr Thr Leu Leu Ala Leu Gly
        355                 360                 365 gcc tat ttc tac tta aag cag aac cac att gac gtc aca gct tac ggt     1152
Ala Tyr Phe Tyr Leu Lys Gln Asn His Ile Asp Val Thr Ala Tyr Gly
    370                 375                 380 tgg ctg cca ctc gca tgc ctc gtt atc tat gtg ttg gga ttc tca atc     1200
Trp Leu Pro Leu Ala Cys Leu Val Ile Tyr Val Leu Gly Phe Ser Ile
385                 390                 395                 400 gga ttc gga ccg att ccg tgg ctc atg tta gga gaa att tta cca tca     1248
Gly Phe Gly Pro Ile Pro Trp Leu Met Leu Gly Glu Ile Leu Pro Ser
```

-continued

```
                      405                 410                 415
aag att aga ggt acg gct gcg tca ttg gca act ggc ttc aac tgg aca        1296
Lys Ile Arg Gly Thr Ala Ala Ser Leu Ala Thr Gly Phe Asn Trp Thr
            420                 425                 430 tgc act ttt att gtt acg aaa aca ttc caa aac att att gac gct atc        1344
Cys Thr Phe Ile Val Thr Lys Thr Phe Gln Asn Ile Ile Asp Ala Ile
                435                 440                 445 tat atg cat gga aca ctt tgg tta ttt gct gtt att tgt ata gga ggc        1392
Tyr Met His Gly Thr Leu Trp Leu Phe Ala Val Ile Cys Ile Gly Gly
        450                 455                 460 tta ttg ttt gtt att ttc ttc gtg cct gag acc aag ggc aaa agt ctc        1440
Leu Leu Phe Val Ile Phe Phe Val Pro Glu Thr Lys Gly Lys Ser Leu
465                 470                 475                 480 gaa gaa att gaa atg aaa ttg acg agc gga tcc cgg agg gtc cgc aat        1488
Glu Glu Ile Glu Met Lys Leu Thr Ser Gly Ser Arg Arg Val Arg Asn
                485                 490                 495 atc agt aaa caa cca gaa aat att tgt taa tga                            1521
Ile Ser Lys Gln Pro Glu Asn Ile Cys
            500                 505

<210> SEQ ID NO 10
<211> LENGTH: 505
<212> TYPE: PRT
<213> ORGANISM: Bombyx mori

<400> SEQUENCE: 10

Met Glu Met Glu Ile Lys Asp Glu Asn Leu Arg Asn Ser Val Pro Phe
1               5                   10                  15

Val Arg Gln Leu Ser Thr Asp Ser Val Lys Thr Lys Thr Glu Tyr Asp
            20                  25                  30

Asn Glu Asp Gly Thr Pro Tyr Lys Ser Thr Thr Gln Lys Leu Phe Leu
        35                  40                  45

Trp Thr Gln Leu Leu Ala Ala Phe Ala Val Ser Val Gly Ser Met Asn
    50                  55                  60

Val Gly Phe Ser Ser Gly Tyr Thr Ser Pro Ala Val Leu Thr Met Asn
65                  70                  75                  80

Ile Thr Leu Asp Ile Thr Lys Glu Glu Ile Thr Trp Val Gly Gly Leu
                85                  90                  95

Met Pro Leu Ala Ala Leu Val Gly Gly Ile Val Gly Gly Pro Leu Ile
            100                 105                 110

Glu Tyr Leu Gly Arg Lys Lys Thr Ile Met Gly Thr Ala Val Pro Phe
        115                 120                 125

Thr Ile Gly Trp Met Leu Ile Ala Asn Ala Ile Asn Val Val Met Val
    130                 135                 140

Phe Ala Gly Arg Val Ile Cys Gly Val Cys Val Gly Ile Val Ser Leu
145                 150                 155                 160

Ala Phe Pro Val Tyr Ile Gly Glu Thr Ile Gln Pro Glu Val Arg Gly
                165                 170                 175

Ala Leu Gly Leu Leu Pro Thr Ala Phe Gly Asn Thr Gly Ile Leu Leu
            180                 185                 190

Ala Phe Leu Val Gly Ser Tyr Leu Asp Trp Ser Asn Leu Ala Phe Phe
        195                 200                 205

Gly Ala Ala Ile Pro Val Pro Phe Phe Leu Leu Met Ile Leu Thr Pro
    210                 215                 220

Glu Thr Pro Arg Trp Tyr Val Ser Lys Ala Arg Val Gln Glu Ala Arg
225                 230                 235                 240
```

```
Lys Ser Leu Arg Trp Leu Arg Gly Lys Asn Val Asn Ile Glu Lys Glu
            245                 250                 255

Met Arg Asp Leu Thr Ile Ser Gln Thr Glu Ser Asp Arg Thr Gly Gly
            260                 265                 270

Asn Ala Phe Lys Gln Leu Phe Ser Lys Arg Tyr Leu Pro Ala Val Met
            275                 280                 285

Ile Ser Leu Gly Leu Met Leu Phe Gln Gln Leu Thr Gly Ile Asn Ala
            290                 295                 300

Val Ile Phe Tyr Ala Ala Ser Ile Phe Gln Met Ser Gly Ser Ser Val
305                 310                 315                 320

Asp Glu Asn Leu Ala Ser Ile Ile Ile Gly Val Val Asn Phe Ile Ser
                    325                 330                 335

Thr Phe Ile Ala Thr Met Leu Ile Asp Arg Leu Gly Arg Lys Val Leu
                    340                 345                 350

Leu Tyr Ile Ser Ser Val Ala Met Ile Thr Thr Leu Leu Ala Leu Gly
                    355                 360                 365

Ala Tyr Phe Tyr Leu Lys Gln Asn His Ile Asp Val Thr Ala Tyr Gly
            370                 375                 380

Trp Leu Pro Leu Ala Cys Leu Val Ile Tyr Val Leu Gly Phe Ser Ile
385                 390                 395                 400

Gly Phe Gly Pro Ile Pro Trp Leu Met Leu Gly Glu Ile Leu Pro Ser
                    405                 410                 415

Lys Ile Arg Gly Thr Ala Ala Ser Leu Ala Thr Gly Phe Asn Trp Thr
                    420                 425                 430

Cys Thr Phe Ile Val Thr Lys Thr Phe Gln Asn Ile Ile Asp Ala Ile
                    435                 440                 445

Tyr Met His Gly Thr Leu Trp Leu Phe Ala Val Ile Cys Ile Gly Gly
            450                 455                 460

Leu Leu Phe Val Ile Phe Phe Val Pro Glu Thr Lys Gly Lys Ser Leu
465                 470                 475                 480

Glu Glu Ile Glu Met Lys Leu Thr Ser Gly Ser Arg Arg Val Arg Asn
                    485                 490                 495

Ile Ser Lys Gln Pro Glu Asn Ile Cys
            500                 505

<210> SEQ ID NO 11
<211> LENGTH: 29
<212> TYPE: PRT
<213> ORGANISM: Artificial
<220> FEATURE:
<223> OTHER INFORMATION: an artificially synthesized peptide sequence
<220> FEATURE:
<221> NAME/KEY: MISC_FEATURE
<222> LOCATION: (2)..(2)
<223> OTHER INFORMATION: "Xaa" in position 2 indicates any hydrophobic
      amino acid
<220> FEATURE:
<221> NAME/KEY: MISC_FEATURE
<222> LOCATION: (6)..(6)
<223> OTHER INFORMATION: "Xaa" in position 6 indicates any hydrophobic
      amino acid
<220> FEATURE:
<221> NAME/KEY: MISC_FEATURE
<222> LOCATION: (7)..(7)
<223> OTHER INFORMATION: "Xaa" in position 7 indicates Serine or
      Alanine
<220> FEATURE:
<221> NAME/KEY: MISC_FEATURE
<222> LOCATION: (10)..(10)
<223> OTHER INFORMATION: "Xaa" in position 10 indicates any
      hydrophobic amino acid
<220> FEATURE:
```

```
<221> NAME/KEY: MISC_FEATURE
<222> LOCATION: (11)..(11)
<223> OTHER INFORMATION: "Xaa" in position 11 indicates Glycine or
      Alanine
<220> FEATURE:
<221> NAME/KEY: MISC_FEATURE
<222> LOCATION: (13)..(13)
<223> OTHER INFORMATION: "Xaa" in position 13 indicates any
      hydrophobic amino acid
<220> FEATURE:
<221> NAME/KEY: MISC_FEATURE
<222> LOCATION: (14)..(14)
<223> OTHER INFORMATION: "Xaa" in position 14 can be any naturally
      occurring amino acid
<220> FEATURE:
<221> NAME/KEY: MISC_FEATURE
<222> LOCATION: (15)..(15)
<223> OTHER INFORMATION: "Xaa" in position 15 indicates Valine or
      Isoleucine
<220> FEATURE:
<221> NAME/KEY: MISC_FEATURE
<222> LOCATION: (17)..(17)
<223> OTHER INFORMATION: "Xaa" in position 17 indicates Phenylalanine
      or Tyrosine
<220> FEATURE:
<221> NAME/KEY: MISC_FEATURE
<222> LOCATION: (18)..(18)
<223> OTHER INFORMATION: "Xaa" in position 18 can be any naturally
      occurring amino acid
<220> FEATURE:
<221> NAME/KEY: MISC_FEATURE
<222> LOCATION: (20)..(20)
<223> OTHER INFORMATION: "Xaa" in position 20 can be any naturally
      occurring amino acid
<220> FEATURE:
<221> NAME/KEY: MISC_FEATURE
<222> LOCATION: (26)..(26)
<223> OTHER INFORMATION: "Xaa" in position 26 indicates Leucine or
      Valine
<220> FEATURE:
<221> NAME/KEY: MISC_FEATURE
<222> LOCATION: (27)..(27)
<223> OTHER INFORMATION: "Xaa" in position 27 indicates Leucine or
      Valine
<220> FEATURE:
<221> NAME/KEY: MISC_FEATURE
<222> LOCATION: (28)..(28)
<223> OTHER INFORMATION: "Xaa" in position 28 indicates Serine or
      Threonine

<400> SEQUENCE: 11

Gln Xaa Leu Ala Ala Xaa Xaa Val Ser Xaa Xaa Ser Xaa Xaa Xaa Gly
1               5                   10                  15

Xaa Xaa Ser Xaa Tyr Thr Ser Pro Ala Xaa Xaa Xaa Met
            20                  25

<210> SEQ ID NO 12
<211> LENGTH: 29
<212> TYPE: PRT
<213> ORGANISM: Polypedilum vanderplanki

<400> SEQUENCE: 12

Gln Ile Leu Ala Ala Ile Ala Val Ser Met Gly Ser Met Val Val Gly
1               5                   10                  15

Phe Ala Ser Ala Tyr Thr Ser Pro Ala Leu Val Ser Met
            20                  25

<210> SEQ ID NO 13
<211> LENGTH: 441
<212> TYPE: PRT
<213> ORGANISM: Polypedilum vanderplanki

<400> SEQUENCE: 13
```

```
Ile Leu Ala Ala Ile Ala Val Ser Met Gly Ser Met Val Gly Phe
1               5                   10                  15

Ala Ser Ala Tyr Thr Ser Pro Ala Leu Val Ser Met Gln Asn Thr Thr
            20                  25                  30

Ile Thr Ser Phe Lys Val Thr Glu Gln Glu Ala Ser Trp Val Gly Gly
        35                  40                  45

Ile Met Pro Leu Ala Gly Leu Ala Gly Gly Ile Ala Gly Gly Pro Phe
    50                  55                  60

Ile Glu Tyr Leu Gly Arg Lys Asn Thr Ile Leu Ala Thr Ala Val Pro
65                  70                  75                  80

Phe Ile Val Ala Trp Leu Leu Ile Ala Phe Ala Asn Ser Ile Trp Met
                85                  90                  95

Val Leu Ala Gly Arg Ala Leu Ser Gly Phe Cys Val Gly Ile Ala Ser
                100                 105                 110

Leu Ser Leu Pro Val Tyr Leu Gly Glu Thr Val Gln Pro Glu Val Arg
            115                 120                 125

Gly Thr Leu Gly Leu Leu Pro Thr Ala Phe Gly Asn Ile Gly Ile Leu
130                 135                 140

Ile Cys Phe Val Ala Gly Lys Tyr Val Asn Trp Ser Gly Leu Ala Phe
145                 150                 155                 160

Ile Gly Ser Ile Leu Pro Ile Pro Phe Met Val Leu Thr Leu Leu Ile
                165                 170                 175

Pro Glu Thr Pro Arg Trp Phe Val Thr Arg Gly Arg Glu Glu Arg Ala
            180                 185                 190

Arg Lys Ala Leu Gln Trp Leu Arg Gly Lys Lys Ala Asp Val Glu Pro
            195                 200                 205

Glu Leu Lys Gly Ile Val Lys Ser His Cys Glu Ala Glu Arg His Ala
210                 215                 220

Ser Gln Asn Ala Ile Phe Asp Leu Met Lys Arg Ser Asn Leu Lys Pro
225                 230                 235                 240

Leu Leu Ile Ala Leu Gly Leu Met Phe Phe Gln Gln Leu Ser Gly Ile
                245                 250                 255

Asn Ala Val Ile Phe Tyr Thr Val Ser Ile Phe Lys Asp Ala Gly Ser
                260                 265                 270

Thr Ile Asp Glu Asn Leu Cys Thr Ile Val Gly Val Val Asn Phe
            275                 280                 285

Gly Ala Thr Phe Phe Ala Thr Val Leu Ile Asp Arg Leu Gly Arg Lys
    290                 295                 300

Ile Leu Leu Tyr Ile Ser Glu Val Ala Met Val Ile Thr Leu Leu Thr
305                 310                 315                 320

Leu Gly Thr Phe Phe Tyr Tyr Lys Asn Ser Gly Asn Asp Val Ser Asn
            325                 330                 335

Ile Gly Trp Leu Pro Leu Ala Ser Phe Val Ile Tyr Val Ile Gly Phe
                340                 345                 350

Ser Ser Gly Val Gly Pro Ile Pro Trp Leu Met Leu Gly Glu Ile Leu
            355                 360                 365

Pro Gly Lys Ile Arg Gly Ser Ala Ala Ser Val Ala Thr Gly Phe Asn
370                 375                 380

Trp Thr Cys Thr Phe Ile Val Thr Lys Thr Phe Ala Asp Ile Val Ala
385                 390                 395                 400

Ala Ile Gly Asn His Gly Ala Phe Trp Phe Phe Gly Val Ile Cys Leu
                405                 410                 415
```

```
-continued

Ile Gly Leu Phe Phe Val Ile Phe Phe Val Pro Glu Thr Gln Gly Lys
                420                 425                 430

Ser Leu Glu Glu Ile Glu Arg Lys Met
        435             440
```